(12) United States Patent
Baroni et al.

(10) Patent No.: US 8,906,924 B2
(45) Date of Patent: Dec. 9, 2014

(54) (HETEROCYCLE/TETRAHYDROPYRIDINE)-(PIPERAZINYL)-1-ALCANONE AND (HETEROCYCLE/DIHYDROPYRROLIDINE)-(PIPERAZINYL)-1-ALCANONE DERIVATIVES, AND USE THEREOF AS P75 INHIBITORS

(71) Applicant: Sanofi, Paris (FR)

(72) Inventors: Marco Baroni, Vanzago-Milano (IT); Francoise Bono, Toulouse (FR); Sandrine Delbary-Gossart, Mauzac (FR); Valentina Vercesi, Vellezo Bellini (IT)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/945,478

(22) Filed: Jul. 18, 2013

(65) Prior Publication Data

US 2013/0303520 A1   Nov. 14, 2013

Related U.S. Application Data

(60) Division of application No. 13/490,905, filed on Jun. 7, 2012, now Pat. No. 8,518,947, which is a continuation of application No. PCT/FR2010/052686, filed on Dec. 13, 2010.

(30) Foreign Application Priority Data

Dec. 14, 2009  (FR) ...................................... 09 06025

(51) Int. Cl.
| | |
|---|---|
| *A61K 31/50* | (2006.01) |
| *A61K 31/501* | (2006.01) |
| *C07D 405/04* | (2006.01) |
| *C07D 487/08* | (2006.01) |
| *C07D 409/04* | (2006.01) |
| *C07D 401/04* | (2006.01) |
| *C07D 401/14* | (2006.01) |
| *C07D 495/04* | (2006.01) |
| *C07D 409/14* | (2006.01) |
| *C07D 405/14* | (2006.01) |

(52) U.S. Cl.
CPC ............ *C07D 487/08* (2013.01); *C07D 405/04* (2013.01); *C07D 409/04* (2013.01); *C07D 401/04* (2013.01); *C07D 401/14* (2013.01); *C07D 495/04* (2013.01); *C07D 409/14* (2013.01); *C07D 405/14* (2013.01)
USPC ............ 514/252.02; 514/252.11; 514/252.14; 514/253.01; 544/238; 544/295; 544/357; 544/360; 544/364

(58) Field of Classification Search
USPC ............. 514/252.02, 252.11, 252.14, 253.01; 544/238, 295, 357, 360, 364
See application file for complete search history.

(56) References Cited

U.S. PATENT DOCUMENTS

| | | | |
|---|---|---|---|
| 6,417,188 B1 | 7/2002 | Jonas et al. | |
| 6,689,797 B2 | 2/2004 | Baroni et al. | |
| 7,294,628 B2 | 11/2007 | Bono et al. | |
| 7,423,039 B2 | 9/2008 | Dos Santos et al. | |
| 7,468,368 B2 | 12/2008 | Bono et al. | |
| 7,652,011 B2 | 1/2010 | Bosch et al. | |
| 8,193,190 B2 | 6/2012 | Baroni et al. | |
| 2009/0270412 A1* | 10/2009 | Hung et al. | ............... 514/253.04 |
| 2011/0144122 A1 | 6/2011 | Baroni et al. | |

FOREIGN PATENT DOCUMENTS

| | | | |
|---|---|---|---|
| WO | WO 97/28140 A1 | 8/1997 | |
| WO | WO 99/01423 A1 | 1/1999 | |
| WO | WO 99/65880 | 12/1999 | |
| WO | WO 9965880 A1 | * 12/1999 | |
| WO | WO 00/51984 A1 | 9/2000 | |
| WO | WO 00/59893 A1 | 10/2000 | |
| WO | WO 00/69829 | 11/2000 | |
| WO | WO 0069829 A1 | * 11/2000 | |
| WO | WO 01/49684 | 7/2001 | |
| WO | WO 0149684 A1 | * 7/2001 | |
| WO | WO 03/104225 A1 | 12/2003 | |
| WO | WO 03/104226 A1 | 12/2003 | |
| WO | WO 03104226 A1 | * 12/2003 | |
| WO | WO 2005/054227 A1 | 6/2005 | |
| WO | WO 2005/054229 A1 | 6/2005 | |
| WO | WO 2006/017443 | 2/2006 | |
| WO | WO 2006017443 A2 | * 2/2006 | |
| WO | WO 2009/150387 A1 | 12/2009 | |

OTHER PUBLICATIONS

R. S. Shah et al., 52 Biomedicine & Pharmacotherapy, 199-207 (2008).*
T. O'Brien et al., 2 The Lancet Neurology, 89-98, 96 (2003).*

(Continued)

*Primary Examiner* — James O Wilson
*Assistant Examiner* — Alexander R Pagano
(74) *Attorney, Agent, or Firm* — Kelly L. Bender

(57) ABSTRACT

The disclosure relates to (heterocycle-tetrahydropyridine)(piperazinyl)-1-alkanone and (heterocycle-dihydropyrrolidine)(piperazinyl)-1-alkanone derivatives of formula (I):

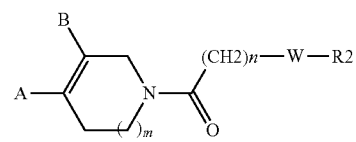

wherein A, B, m, n, W, and R2 are as defined in the disclosure; to the methods of preparing said derivatives, and to the therapeutic uses thereof.

6 Claims, No Drawings

(56) References Cited

OTHER PUBLICATIONS

C.D. Hahn et al., Diseases of the Peripheral Nervous System in, The Central Nervous System in Pediatric Critical Illness and Injury (2009).*
M. Meriggioli et al. The Lancet Neurology 475-490 (2009).*
J.L. Melnick, Eteroviruses in, Neuropathogenic Viruses and Immunity (S. Specter et al., ed., 1992).*
M.R. Lunn et al., 371 The Lancet, 2120-2133 (2008).*
J. Sobel, 41 Clinical Infectious Diseases, 1167-1173 (2005).*
E.A. Hunsperger et al., 12 Journal of NeuroVirology, 129-139 (2006).*
R.C. Hughes et al., 366 The Lancet, 1653-1666 (2005).*
D. Mitchell et al., 369 The Lancet, 2031-2041 (2007).*
H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
C.K. Underwood et al., 40 The International Journal of Biochemistry & Cell Biology, 1664-1668 (2008).*
H. Girouard et al., 100 Journal of Applied Physiology, 328-335, 332 (2006).*
J. Fombonne et al., 65 Annals of Neurology, 294-303 (2009).*
P.A. LeWitt, 359 New England Journal of Medicine, 2468-2473 (2008).*
A. Schapira, 30 Trends in Pharmacological Sciences, 41-47 (2009).*
L. Wijesekera et al., 4 Orphanet Journal of Rare Diseases, (2009).*
C. Zuccoato, 18 Brain Pathology, 225-230 (2007).*
Y-Q Wang et al., 53 Neurochemistry International, 56-62 (2008).*
S. Judge et al., 111 Pharmacology & Therapeutics, 224-259 (2006).*
V. Brinkmann et al., 9 Nature Reviews | Drug Discovery, 883-897 (2010).*
U.S. Appl. No. 13/473,885, filed May 17, 2012, Baroni, et al.
U.S. Appl. No. 13/490,904, filed Jun. 7, 2012, Baroni.
U.S. Appl. No. 13/556,328, filed Jul. 24, 2012, Baroni, et al.
CAS RN: 1087792-03-7, Database Chemcats Online, Chemical Abstracts Service, Database Accession no. 0000883057. Order Number: T6260-161, Enamine Screening Library, (2009).
Della-Blanca, et al., Neurotrophin p75 Receptor is Involved in Neuronal Damage by Prion Peptide-(106-126), The Journal of Biological Chemistry, vol. 276, No. 42. (2001), pp. 38929-38933.
Friedman, et al., Neurotrophin Signaling Via Trks and p75, Experimental Cell Research, vol. 253, pp. 131-142, (1999).
Fukui, et al., Low Affinity NGF Receptor (p75 Neurotrophin Receptor) Inhibitory Antibody Reduces Pain Behavior and CGRP Expression in DRG in the Mouse Sciatic Nerve Crush Model, journal of Orthopaedic Research, (2010), vol. 28, No. 3, pp. 279-283.
Kendall, et al., P75 Neurotrophin Receptor Signaling Regulates Hepatic Myofibroblast Proliferation and Apoptosis in Recovery From Rodent Liver Fibrosis, Hepatology, (2009), vol. 49, No. 3, pp. 901-910.
Longo, et al., Small Molecule Neurotrophin Receptor Ligands: Novel Strategies for Targeting Alzheimer's Disease Mechanisms, Current Alzheimer Research, (2007), vol. 4, pp. 503-506.
Lowry, et al., A Potential Role for the p75 Low-Affinity Neurotrophin Receptor in Spinal Motor Neuron Degeneration in Murine and Human Amyotrophic Lateral Sclerosis, Amyotroph. Lateral. Scler. (2001), vol. 2, pp. 127-134.
Obata, et al., Suppression of the p75 Neurotrophin Receptor in Uninjured Sensory Neurons Reduces Neuropathic Pain After Nerve injury, The Journal of Neuroscience, (2006). vol. 26, No. 46, pp. 11974-11986.
Perlman, et al., Evidence for the Rapid Onset of Apoptosis in Medial Smooth Muscle Cells After Balloon Injury, Circulation, (1997), vol. 95, pp. 981-987.
Rabizadeh, et al., Expression of the Low-Affinity Nerve Growth Factor Receptor Enhances B-Amyloid Peptide Toxicity, Proc. Nati. Acad. Sci. USA, vol. 91, pp. 10703-10706, (1994).
Raychaudhuri, et al., Role of NGF and Neurogenic inflammation in the Pathogenesis of Psoriasis, Progress in Brain Research, vol. 146, pp. 433-437, (2004).
Rihl, et al., Involvement of Neurotrophins and Their Receptors in Spondyloarthritis Synovitis: Relation to inflammation and Response to Treatment, Ann Rheum Die, (2005), vol. 64, pp. 1542-1549.
Roux, et al., p75 Neurotrohpin Receptor Expression is Induced in Apoptotic Neurons After Seizure, The Journal of Neuroscience, (1999), vol. 19, No. 16, pp. 6887-6896.
Saragovi, et al., Small Molecule and Protein-Based Neurotrophic Ligands: Agonists and Antagonists as Therapeutic Agents, Exp. Opin. Ther. Patents, vol. 9(6), pp. 737-751 (1999).
Tokuoka, et al., Disruption of Antigen-Induced Airway Inflammation and Airway Hyper-Responsiveness in Low Affinity Neurotrophin p75 Gene Deficient Mice, British Journal of Pharmacology, (2001), vol. 134, pp. 1580-1586.
Watanabe, et al., The p75 Receptor Is Associated With Inflammatory Thermal Hypersensitivity, Journal of Neuroscience Research, vol. 86, pp. 3566-3574, (2008).
Zhu, et al., Up-Regulation of p75 Neurotrophin Receptor (P75NTR) Is Associated With Apoptosis in Chronic Pancreatitis, Digestive Diseases and Sciences, vol. 48, No. 4, (2003), pp. 717-725.
CAS RN: 1183620-64-5, 2-Chloro-1-(5,6,7,8-tetrahydro-1,6-naphthyridin-6-yl)ethan-1-one, Database Chemcats (Online), Database Accession No. 2096188618 (2009).
CAS RN: 1179621-56-7, 3-Chloro-1-(5,6,7,8-tetrahydro-1,6-naphthyridirt-6-yl)propan-1-one, Database Chemcats (Online), Database Accession No. 2096188619 (2009).
International Search Report for WO2011/080445 dated Jul. 7, 2011.
Chaldakov, G. N., at al., Neurotrophin Presence in Human Coronary Atherosclerosis and Metabolic Syndrome: a Role for NGF and BDNF in Cardiovascular Disease, Progress in Brain Research, vol. 146, pp. 279-289, (2004).
Fuji!, et al., P75NTR as a Therapeutic Target for Neuropsychiatric Diseases, Current Molecular Pharmacology, (2009), vol. 2, pp. 70-76.
Schor, The P75 Neurotrophin Receipt in Human Development and Disease, Progress in Neurobiology, vol. 77, (2005), pp. 201-214.
Zeng, et al., Roles of P75NTR in the Pathogenesis of Alzheimer's Disease: A Novel Therapeutic Target, Biochemical Pharmacology, vol. 82, (2011), pp. 1500-1509.
U.S. Appl. No. 13/556,328—Non-Final Office Action dated Dec. 24, 2013.

* cited by examiner

(HETEROCYCLE/TETRAHYDROPYRIDINE)-(PIPERAZINYL)-1-ALCANONE AND (HETEROCYCLE/DIHYDROPYRROLIDINE)-(PIPERAZINYL)-1-ALCANONE DERIVATIVES, AND USE THEREOF AS P75 INHIBITORS

The present invention relates to (heterocycle-tetrahydropyridine)(piperazinyl)-1-alkanone and (heterocycle-dihydropyrrolidine)(piperazinyl)-1-alkanone derivatives, to their preparation and to their therapeutic use.

The compounds according to the present invention have affinity for the $p75^{NTR}$ receptor of neurotrophins.

Neurotrophins belong to a family of proteins especially having cell survival and differentiation as a biological effect.

The $p75^{NTR}$ receptor, a receptor of all neurotrophins, is a transmembrane glycoprotein of the tumor necrosis factor (TNF) receptor family (W. J. Friedman and L. A. Greene, Exp. Cell. Res., 1999, 253, 131-142). The $p75^{NTR}$ receptor is expressed in several cell types, and several biological functions are attributed thereto: firstly, modulation of the affinity of neurotrophins for the tyrosine kinase (trk) receptors; secondly, in the absence of trk, induction of a cell death signal by apoptosis. Moreover, the neurotrophin precursors, pro-neurotrophins, are capable of binding to $p75^{NTR}$ with high affinity, and are considered as powerful $p75^{NTR}$-dependent apoptosis inducers in neurons and certain cell lines.

In the central nervous system, numerous studies show that apoptosis occurs in several pathologies, such as amyotrophic lateral sclerosis, multiple sclerosis, Alzheimer's disease, Parkinson's disease, Huntington's disease and prion diseases. $p75^{NTR}$ is also known to be overexpressed in various types of neurodegenerative disease, for example Alzheimer's disease and amyotrophic lateral sclerosis (ALS) (Longo F. M. et al., Curr. Alzheimer Res. 2007; 4: 503-506; Lowry K. S. et al., Amyotroph. Lateral. Scler. Other. Motor. Neuron. Disord. 2001; 2:127-34).

Results suggest that $p75^{NTR}$ may play a predominant role in mechanisms leading to neuronal death via post-ischemic apoptosis (P. P. Roux et al., J. Neurosci., 1999, 19, 6887-6896).

Results (V. Della-Bianca et al., J. Biol. Chem., 2001, 276: 38929-33) (S. Rabizadeh et al., Proc. Natl. Acad. Sci. USA, 1994, 91, 10703-10706) support the hypothesis according to which $p75^{NTR}$ plays an important role in neuronal death induced by the infectious prion protein (transmissible spongiform encephalopathy) or by the β-amyloid protein (Alzheimer's disease).

The $p75^{NTR}$ receptor is also associated with the Nogo receptor and involved in the signaling of the inhibitory effects of these myelin proteins with respect to axonal growth. As a result, the $p75^{NTR}$ receptor plays a major role in regulating neuronal plasticity and in neuron-glia interactions and thus represents a therapeutic target of choice for promoting nerve regeneration.

Beyond the nervous system and neurodegenerative diseases, it has been suggested that $p75^{NTR}$ may play a role in cardiovascular diseases such as atherosclerosis and myocardial ischemia (M. L. Bochaton-Pialat et al., Am. J. Pathol., 1995, 146, 1-6; H. Perlman, Circulation, 1997, 95, 981-987). Recent studies show an increase in the expression of $p75^{NTR}$ and of neurotrophins, and massive apoptosis in atherosclerosis lesions.

Several studies also suggest that $p75^{NTR}$ is an inflammation mediator (Rihl M. et al., Ann. Rheum. Dis. 2005; 64(11): 1542-9; Raychaudhuri S. P. et al., Prog. Brain. Res. 2004; 146: 433-7, Tokuoka S. et al., Br. J. Pharmacol. 2001, 134: 1580-1586).

$p75^{NTR}$ is also described as playing an important role in inflammatory pain. Specifically, lesion of the nerve is thought to selectively increase the expression and axonal transport of $p75^{NTR}$, involved in the induction of neuropathic pain. Furthermore, the use of $p75^{NTR}$-specific antibodies or of antisense oligodeoxynucleotide capable of blocking the activity of the receptor in vivo is thought to be capable of reversing neuropathic pain (heat- and cold-induced hyperalgesia and mechanical allodynia) induced in rats after lesion of the L5 spinal nerve (Obata K. et al., J. Neurosci. 2006; 26: 11974-11986). An anti-$p75^{NTR}$ neutralizing antibody considerably reduces the inflammatory pain induced by the injection of adjuvant into the arch of the paw in mice, and also in a model of sciatic nerve crush in mice (Watanabe T. et al., J. Neurosci. Res. 2008; 86: 3566-357; Fukui Y. et al., J Orthop Res. 2010; 28(3): 279-83).

The expression of $p75^{NTR}$ is also described in chronic pancreatitis, with an involvement in apoptosis of the exocrine and endocrine pancreas (Zhu Z. et al., Dig. Dis. Sci. 2003; 48 (4): 717-25).

Other reports have also described the importance of $p75^{NTR}$ in the development of hepatic fibrosis (Kendall T. J. et al., Hepatology. 2009; 49 (3): 901-10).

$p75^{NTR}$ also plays a critical role in tumor biology.

Many compounds are known for interacting with the trkA/NGF/$p75^{NTR}$ system or for having activity of NGF (nerve growth factor) type. Thus, patent application WO 00/59893 describes substituted pyrimidine derivatives with activity of NGF type and/or which increase the NGF activity on PC12 cells.

One subject of the present invention is compounds corresponding to formula (I):

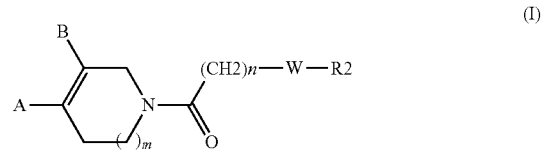

in which:
n represents 1 or 2;
m represents 0 or 1;
A represents a fused heterocyclic group of formula (Y)

and B represents a hydrogen atom;
or
A represents a hydrogen atom; and
B represents a fused heterocyclic group of formula (Y)

The fused heterocycle of formula Y may be attached to the rest of the molecule via any of the available carbon atoms, and in which:

U completes:
either an aromatic or saturated 6-atom nucleus, containing one or two nitrogen atoms, the nucleus possibly being substituted with one or two halogen atoms, one or two (C1-C4)alkyl or (C1-C4)alkoxy groups, or one or two perfluoroalkyl radicals;
or an aromatic or saturated 5-atom nucleus, containing a nitrogen, oxygen or sulfur atom, the nucleus possibly being substituted with one or two groups (C1-C4) alkyl;

X and X1 represent CH or N;

R and R1 located on any of the available positions, independently represent a hydrogen atom, a halogen atom, a group (C1-C4)alkyl, (C1-C4)alkoxy, a perfluoroalkyl or trifluoromethoxy radical, a cyano or a group COOH, COOalkyl, CONR3R4 or NHCOR3;

—W— is a nitrogenous heterocycle chosen from:

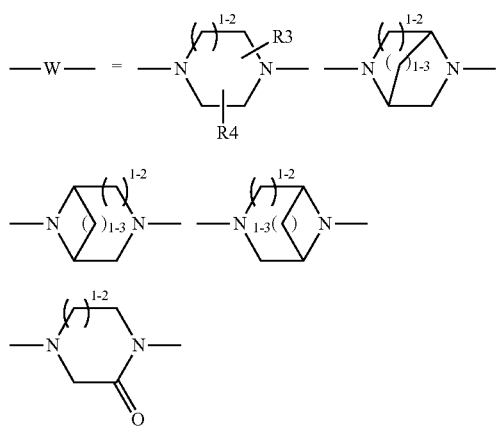

1-2 represents 1 or 2;
1-3 represents 1, 2 or 3;
R2 represents a group of formula:

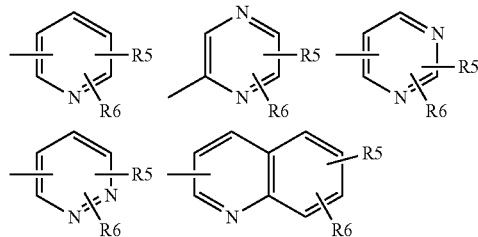

in which R5 and R6, located on any of the available positions, independently represent a hydrogen atom, a halogen atom, a group (C1-C4)alkyl or (C1-C4) alkoxy, a trifluoromethyl or trifluoromethoxy radical, a cyano or a group COOH, COOalkyl, COOcycloalkyl, SOalkyl, SO₂alkyl, CONR3R4, NR3R4 or NHCOR3;

or one of the groups R5 and R6 may also represent a heterocycle chosen from:

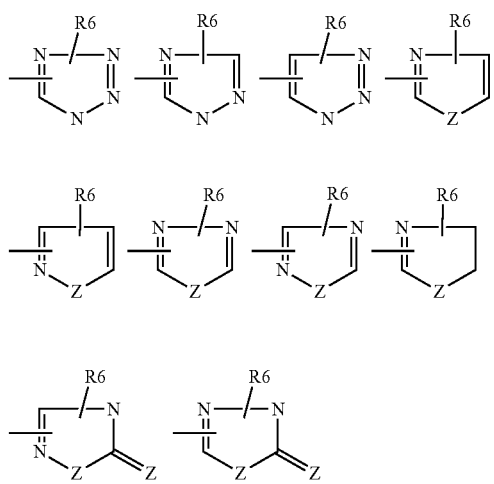

Z represents an oxygen or sulfur atom;

R3 and R4 represent a hydrogen or a group C1-C6 alkyl.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

In the context of the present invention, the following definitions apply:

a halogen atom: a fluorine, a chlorine, a bromine or an iodine;

an alkyl group: a saturated, linear, branched or cyclic aliphatic group. Examples that may be mentioned include a group (C1-C4)alkyl which may represent a methyl, ethyl, propyl, isopropyl, butyl, isobutyl, tert-butyl, cyclopropyl or cyclobutyl;

a fluoroalkyl group: an alkyl group in which one or more hydrogen atoms have been replaced with a fluorine atom;

a perfluoroalkyl group: an alkyl group in which all the hydrogen atoms have been replaced with a fluorine atom, for example trifluoroalkyl;

an alkoxy group: a radical —O-alkyl in which the alkyl group is as defined previously;

a perfluoroalkoxy group: an alkoxy group in which all the hydrogen atoms have been replaced with a fluorine atom, for example trifluoroalkoxy;

a cycloalkyl group: a cyclic alkyl group. Examples that may be mentioned include cyclopropyl, methylcyclopropyl, cyclobutyl, cyclopentyl, cyclohexyl, etc., groups.

Among the compounds of formula (I) that are subjects of the invention, another group of compounds is formed by the compounds of formula (I) in which:

n represents 1 or 2; and/or m represents 0 or 1; and/or

A represents a fused heterocyclic group of formula (Y)

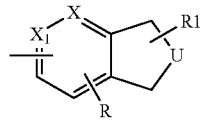
(Y)

and B represents a hydrogen atom;

or

A represents a hydrogen atom;

and B represents a fused heterocyclic group of formula (Y)

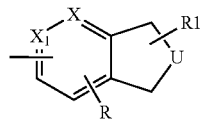
(Y)

the fused heterocycle of formula Y possibly being attached to the rest of the molecule via any of the available carbon atoms of the benzene nucleus;

U completes:
either an aromatic or saturated 6-atom nucleus, containing one or two nitrogen atoms, the nucleus possibly being substituted with one or two halogen atoms, one or two (C1-C4)alkyl or (C1-C4)alkoxy groups, or one or two perfluoroalkyl radicals;

or an aromatic or saturated 5-atom nucleus, containing a nitrogen, oxygen or sulfur atom, the nucleus possibly being substituted with one or two groups (C1-C4) alkyl; and/or X and X1 represent CH or N; and/or R and R1, located on any of the available positions, independently represent a hydrogen atom, a halogen atom or a group (C1-C4)alkyl or COOalkyl; and/or —W— is a nitrogenous heterocycle chosen from:

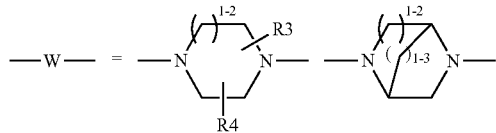

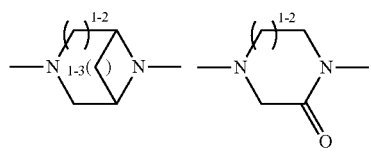

or alternatively

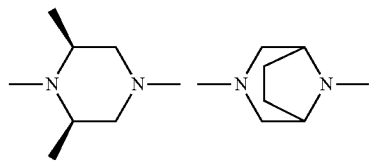

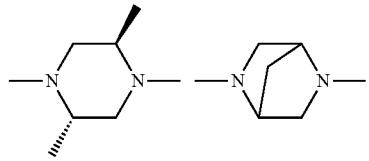

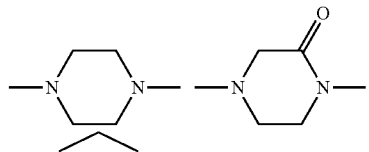

and/or;

R2 represents a group of formula:

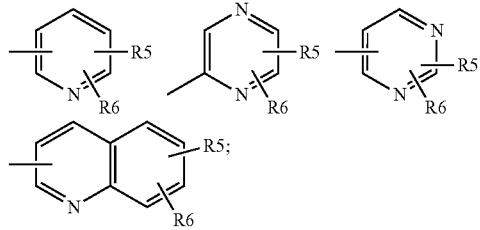

and/or

R5 and R6, located on any of the available positions, independently represent a halogen atom, a trifluoromethyl radical or a group COOH, COOalkyl or COOcycloalkyl;

or one of the groups R5 and R6 may also represent a heterocycle chosen from:

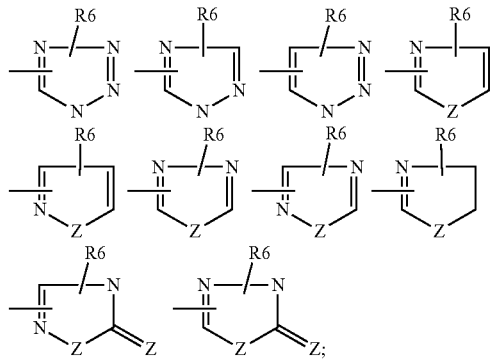

and/or

Z represents an oxygen or sulfur atom; and/or

R3 and R4 represent a hydrogen or a methyl group.

Among the compounds of formula (I) that are subjects of the invention, mention may be made especially of the following compounds:

Compound 1: 1-(4-benzo[b]thiophen-7-yl-3,6-dihydro-2H-pyridin-1-yl)-2-(3,5-dimethyl-2,3,5,6-tetrahydro[1,2']bipyrazinyl-4-yl)ethanone;
Compound 2: 1-(4-benzo[b]thiophen-7-yl-3,6-dihydro-2H-pyridin-1-yl)-2-(8-pyrimidin-2-yl-3,8-diazabicyclo[3.2.1]oct-3-yl)ethanone;
Compound 3: 1-(4-benzo[b]thiophen-5-yl-3,6-dihydro-2H-pyridin-1-yl)-2-(8-pyrimidin-2-yl-3,8-diazabicyclo[3.2.1]oct-3-yl)ethanone;
Compound 4: 1-(4-benzo[b]thiophen-7-yl-3,6-dihydro-2H-pyridin-1-yl)-2-[(2S,6R)-2,6-dimethyl-4-(5-trifluoromethylpyridin-2-yl)piperazin-1-yl]ethanone;
Compound 5: 1-(4-benzo[b]thiophen-5-yl-3,6-dihydro-2H-pyridin-1-yl)-2-((2S,5R)-2,5-dimethyl-2,3,5,6-tetrahydro-[1,2']bipyrazinyl-4-yl)ethanone;
Compound 6: 1-(4-benzo[b]thiophen-7-yl-3,6-dihydro-2H-pyridin-1-yl)-2-((2S,5R)-2,5-dimethyl-2,3,5,6-tetrahydro-[1,2']bipyrazinyl-4-yl)ethanone;
Compound 7: 1-(4-benzo[b]thiophen-5-yl-3,6-dihydro-2H-pyridin-1-yl)-2-[(2S,6R)-2,6-dimethyl-4-(5-trifluoromethylpyridin-2-yl)piperazin-1-yl]ethanone;
Compound 8: 1-(4-benzo[b]thiophen-7-yl-3,6-dihydro-2H-pyridin-1-yl)-2-[8-(5-trifluoromethylpyridin-2-yl)-3,8-diazabicyclo[3.2.1]oct-3-yl]ethanone;
Compound 9: 1-(4-benzo[b]thiophen-7-yl-3,6-dihydro-2H-pyridin-1-yl)-2-[(2R,5S)-2,5-dimethyl-4-(5-trifluoromethylpyridin-2-yl)piperazin-1-yl]ethanone;
Compound 10: 2-[(2S,6R)-2,6-dimethyl-4-(5-trifluoromethylpyridin-2-yl)piperazin-1-yl]-1-[4-(2-methylbenzo[b]thiophen-7-yl)-3,6-dihydro-2H-pyridin-1-yl]ethanone;
Compound 11: 2-[(2S,6R)-2,6-dimethyl-4-(5-trifluoromethylpyridin-2-yl)piperazin-1-yl]-1-[4-(2-propylbenzo[b]thiophen-7-yl)-3,6-dihydro-2H-pyridin-1-yl]ethanone;
Compound 12: 1-(4-benzo[b]thiophen-7-yl-3,6-dihydro-2H-pyridin-1-yl)-2-[5-(5-trifluoromethylpyridin-2-yl)-2,5-diazabicyclo[2.2.1]hept-2-yl]ethanone;
Compound 13: 1-(4-benzo[b]thiophen-6-yl-3,6-dihydro-2H-pyridin-1-yl)-2-[(2R,5S)-2,5-dimethyl-4-(5-trifluoromethylpyridin-2-yl)piperazin-1-yl]ethanone;
Compound 14: 1-(4-benzofuran-7-yl-3,6-dihydro-2H-pyridin-1-yl)-2-[(2R,5S)-2,5-dimethyl-4-(5-trifluoromethylpyridin-2-yl)piperazin-1-yl]ethanone;
Compound 15: 1-[4-(2-methylbenzo[b]thiophen-5-yl)-3,6-dihydro-2H-pyridin-1-yl]-2-(8-pyrimidin-2-yl-3,8-diazabicyclo[3.2.1]oct-3-yl)ethanone;
Compound 16: 1-[4-(2-methylbenzo[b]thiophen-5-yl)-3,6-dihydro-2H-pyridin-1-yl]-2-[4-(5-trifluoromethylpyridin-2-yl)piperazin-1-yl]ethanone;
Compound 17: 4-{2-[4-(2-methylbenzo[b]thiophen-5-yl)-3,6-dihydro-2H-pyridin-1-yl]-2-oxoethyl}-1-(5-trifluoromethylpyridin-2-yl)piperazin-2-one;
Compound 18: 2-[(2S,6R)-2,6-dimethyl-4-(5-trifluoromethylpyridin-2-yl)piperazin-1-yl]-1-[4-(2-methylbenzo[b]thiophen-5-yl)-3,6-dihydro-2H-pyridin-1-yl]ethanone;
Compound 19: 1-(4-benzo[b]thiophen-7-yl-3,6-dihydro-2H-pyridin-1-yl)-2-((2S,6R)-2,6-dimethyl-4-quinolin-2-ylpiperazin-1-yl)ethanone;
Compound 20: 1-(4-quinolin-8-yl-3,6-dihydro-2H-pyridin-1-yl)-2-[4-(5-trifluoromethylpyridin-2-yl)piperazin-1-yl]ethanone;
Compound 21: 1-[4-(2,3-dihydrobenzo[1,4]dioxin-6-yl)-3,6-dihydro-2H-pyridin-1-yl]-2-[4-(5-trifluoromethylpyridin-2-yl)piperazin-1-yl]ethanone;
Compound 22: 2-[8-(5-fluoropyrimidin-2-yl)-3,8-diazabicyclo[3.2.1]oct-3-yl]-1-[4-(2-methylbenzo[b]thiophen-5-yl)-3,6-dihydro-2H-pyridin-1-yl]ethanone;
Compound 23: 1-(4-benzofuran-7-yl-3,6-dihydro-2H-pyridin-1-yl)-2-[8-(5-fluoropyrimidin-2-yl)-3,8-diazabicyclo[3.2.1]oct-3-yl]ethanone;
Compound 24: 1-[4-(2,3-dihydrobenzo[1,4]dioxin-6-yl)-3,6-dihydro-2H-pyridin-1-yl]-2-[8-(5-fluoropyrimidin-2-yl)-3,8-diazabicyclo[3.2.1]oct-3-yl]ethanone;
Compound 25: 2-[8-(5-fluoropyrimidin-2-yl)-3,8-diazabicyclo[3.2.1]oct-3-yl]-1-(4-thieno[3,2-c]pyridin-4-yl-3,6-dihydro-2H-pyridin-1-yl)ethanone;
Compound 26: 1-(4-benzofuran-3-yl-3,6-dihydro-2H-pyridin-1-yl)-2-[8-(5-fluoropyrimidin-2-yl)-3,8-diazabicyclo[3.2.1]oct-3-yl]ethanone;
Compound 27: 2-[8-(5-fluoropyrimidin-2-yl)-3,8-diazabicyclo[3.2.1]oct-3-yl]-1-[4-(1H-indol-3-yl)-3,6-dihydro-2H-pyridin-1-yl]ethanone;
Compound 28: 1-[4-(6-fluoro-1H-indol-3-yl)-3,6-dihydro-2H-pyridin-1-yl]-2-[8-(5-fluoropyrimidin-2-yl)-3,8-diazabicyclo[3.2.1]oct-3-yl]ethanone;
Compound 29: 1-(4-benzo[b]thiophen-3-yl-3,6-dihydro-2H-pyridin-1-yl)-2-[8-(5-fluoropyrimidin-2-yl)-3,8-diazabicyclo[3.2.1]oct-3-yl]ethanone;
Compound 30: 4-{2-[4-(1H-indol-3-yl)-3,6-dihydro-2H-pyridin-1-yl]-2-oxoethyl}-1-(5-trifluoromethylpyridin-2-yl)piperazin-2-one;
Compound 31: 4-[2-(4-benzo[b]thiophen-7-yl-3,6-dihydro-2H-pyridin-1-yl)-2-oxoethyl]-1-(5-trifluoromethylpyridin-2-yl)piperazin-2-one;
Compound 32: 4-[2-(4-benzofuran-7-yl-3,6-dihydro-2H-pyridin-1-yl)-2-oxoethyl]-1-(5-trifluoromethylpyridin-2-yl)piperazin-2-one;
Compound 33: 1-(4-benzofuran-7-yl-3,6-dihydro-2H-pyridin-1-yl)-2-[4-(5-trifluoromethylpyridin-2-yl)piperazin-1-yl]ethanone;
Compound 34: 1-(4-benzofuran-7-yl-3,6-dihydro-2H-pyridin-1-yl)-2-[(2S,6R)-2,6-dimethyl-4-(5-trifluoromethylpyridin-2-yl)piperazin-1-yl]ethanone;
Compound 35: 1-(4-benzofuran-7-yl-3,6-dihydro-2H-pyridin-1-yl)-2-((2S,6R)-2,6-dimethyl-4-pyrimidin-5-ylpiperazin-1-yl)ethanone;
Compound 36: 1-(4-benzofuran-7-yl-3,6-dihydro-2H-pyridin-1-yl)-2-[(2S,6R)-4-(5-fluoropyrimidin-2-yl)-2,6-dimethylpiperazin-1-yl]ethanone;
Compound 37: 1-(4-benzofuran-7-yl-3,6-dihydro-2H-pyridin-1-yl)-2-[(2S,6R)-2,6-dimethyl-4-(6-trifluoromethylpyridin-3-yl)piperazin-1-yl]ethanone;
Compound 38: 2-[(2S,6R)-4-(5-fluoropyrimidin-2-yl)-2,6-dimethylpiperazin-1-yl]-1-[4-(2-methylbenzo[b]thiophen-5-yl)-3,6-dihydro-2H-pyridin-1-yl]ethanone;
Compound 39: 2-[(2S,6R)-2,6-dimethyl-4-(6-trifluoromethylpyridin-3-yl)piperazin-1-yl]-1-[4-(2-methylbenzo[b]thiophen-5-yl)-3,6-dihydro-2H-pyridin-1-yl]ethanone;
Compound 40: 2-((2S,6R)-2,6-dimethyl-4-pyrimidin-5-ylpiperazin-1-yl)-1-[4-(2-methylbenzo[b]thiophen-5-yl)-3,6-dihydro-2H-pyridin-1-yl]ethanone;
Compound 41: 1-(4-benzo[b]thiophen-5-yl-3,6-dihydro-2H-pyridin-1-yl)-2-((2S,6R)-2,6-dimethyl-4-pyrimidin-5-ylpiperazin-1-yl)ethanone;
Compound 42: 1-(4-benzo[b]thiophen-5-yl-3,6-dihydro-2H-pyridin-1-yl)-2-[(2S,6R)-4-(5-fluoropyrimidin-2-yl)-2,6-dimethylpiperazin-1-yl]ethanone;
Compound 43: 4-[2-(4-benzo[b]thiophen-5-yl-3,6-dihydro-2H-pyridin-1-yl)-2-oxoethyl]-1-(5-trifluoromethylpyridin-2-yl)piperazin-2-one;
Compound 44: 1-[4-(2,3-dihydrobenzo[1,4]dioxin-6-yl)-3,6-dihydro-2H-pyridin-1-yl]-2-[(2S,6R)-4-(5-fluoropyrimidin-2-yl)-2,6-dimethylpiperazin-1-yl]ethanone;

Compound 45: 1-[4-(2,3-dihydrobenzo[1,4]dioxin-6-yl)-3,6-dihydro-2H-pyridin-1-yl]-2-[(2S,6R)-2,6-dimethyl-4-(6-trifluoromethylpyridin-3-yl)piperazin-1-yl]ethanone;

Compound 46: 1-(4-benzo[b]thiophen-5-yl-3,6-dihydro-2H-pyridin-1-yl)-2-[4-(5-trifluoromethylpyridin-2-yl)piperazin-1-yl]ethanone;

Compound 47: 1-(4-benzo[b]thiophen-5-yl-3,6-dihydro-2H-pyridin-1-yl)-2-[(2S,6R)-2,6-dimethyl-4-(6-trifluoromethylpyridin-3-yl)piperazin-1-yl]ethanone;

Compound 48: 6-{(3S,5R)-4-[2-(4-benzo[b]thiophen-4-yl-3,6-dihydro-2H-pyridin-1-yl)-2-oxoethyl]-3,5-dimethylpiperazin-1-yl}nicotinic acid;

Compound 49: 4-{2-[4-(2,3-dihydrobenzo[1,4]dioxin-6-yl)-3,6-dihydro-2H-pyridin-1-yl]-2-oxoethyl}-1-(5-trifluoromethylpyridin-2-yl)piperazin-2-one;

Compound 50: 1-(4-benzo[b]thiophen-7-yl-3,6-dihydro-2H-pyridin-1-yl)-2-[4-5-trifluoromethylpyridin-2-yl)piperazin-1-yl]ethanone;

Compound 51: Methyl 6-{(3S,5R)-4-[2-(4-benzofuran-7-yl-3,6-dihydro-2H-pyridin-1-yl)-2-oxoethyl]-3,5-dimethylpiperazin-1-yl}nicotinate;

Compound 52: Methyl 6-{(3S,5R)-4-[2-(4-benzo[b]thiophen-5-yl-3,6-dihydro-2H-pyridin-1-yl)-2-oxoethyl]-3,5-dimethylpiperazin-1-yl}nicotinate;

Compound 53: 1-(4-benzo[b]thiophen-7-yl-3,6-dihydro-2H-pyridin-1-yl)-2-[(2S,6R)-4-(5-fluoropyrimidin-2-yl)-2,6-dimethylpiperazin-1-yl]ethanone;

Compound 54: 1-(4-benzo[b]thiophen-7-yl-3,6-dihydro-2H-pyridin-1-yl)-2-[(2S,6R)-2,6-dimethyl-4-(6-trifluoromethylpyridin-3-yl)piperazin-1-yl]ethanone;

Compound 55: 1-(4-benzo[b]thiophen-7-yl-3,6-dihydro-2H-pyridin-1-yl)-2-((2S,6R)-2,6-dimethyl-4-pyrimidin-5-ylpiperazin-1-yl)ethanone;

Compound 56: 6-{(3S,5R)-4-[2-(4-benzo[b]thiophen-5-yl-3,6-dihydro-2H-pyridin-1-yl)-2-oxoethyl]-3,5-dimethylpiperazin-1-yl}nicotinic acid;

Compound 57: 6-{(3S,5R)-4-[2-(4-benzofuran-7-yl-3,6-dihydro-2H-pyridin-1-yl)-2-oxoethyl]-3,5-dimethylpiperazin-1-yl}nicotinic acid;

Compound 58: Methyl 6-{(3S,5R)-4-[2-(4-benzo[b]thiophen-7-yl-3,6-dihydro-2H-pyridin-1-yl)-2-oxoethyl]-3,5-dimethylpiperazin-1-yl}nicotinate;

Compound 59: 6-{(3S,5R)-4-[2-(4-benzo[b]thiophen-7-yl-3,6-dihydro-2H-pyridin-1-yl)-2-oxoethyl]-3,5-dimethylpiperazin-1-yl}nicotinic acid;

Compound 60: 4-[2-(4-benzofuran-5-yl-3,6-dihydro-2H-pyridin-1-yl)-2-oxoethyl]-1-(5-trifluoromethylpyridin-2-yl)piperazin-2-one;

Compound 61: Methyl 6-((3S,5R)-3,5-dimethyl-4-{2-[4-(2-methylbenzo[b]thiophen-5-yl)-3,6-dihydro-2H-pyridin-1-yl]-2-oxoethyl}piperazin-1-yl)nicotinate;

Compound 62: 6-((3S,5R)-3,5-dimethyl-4-{2-[4-(2-methylbenzo[b]thiophen-5-yl)-3,6-dihydro-2H-pyridin-1-yl]-2-oxoethyl}piperazin-1-yl)nicotinic acid;

Compound 63: 1-(5-benzofuran-7-yl-3,6-dihydro-2H-pyridin-1-yl)-2-[(2S,6R)-2,6-dimethyl-4-(5-trifluoromethylpyridin-2-yl)piperazin-1-yl]ethanone;

Compound 64: Ethyl 6-{(3S,5R)-4-[2-(4-benzofuran-7-yl-3,6-dihydro-2H-pyridin-1-yl)-2-oxoethyl]-3,5-dimethylpiperazin-1-yl}nicotinate;

Compound 65: Methyl 6-{3-[2-(4-benzofuran-7-yl-3,6-dihydro-2H-pyridin-1-yl)-2-oxoethyl]-3,8-diazabicyclo[3.2.1]oct-8-yl}nicotinate;

Compound 66: Methyl 7-(1-{2-[(2S,6R)-2,6-dimethyl-4-(5-trifluoromethylpyridin-2-yl)piperazin-1-yl]acetyl}-1,2,3,6-tetrahydropyridin-4-yl)benzo[b]thiophene-2-carboxylate;

Compound 67: Methyl 5-(1-{2-[(2S,6R)-2,6-dimethyl-4-(5-trifluoromethylpyridin-2-yl)piperazin-1-yl]acetyl}-1,2,3,6-tetrahydropyridin-4-yl)benzo[b]thiophene-2-carboxylate;

Compound 68: 2-[(2S,6R)-2,6-dimethyl-4-(5-trifluoromethylpyridin-2-yl)piperazin-1-yl]-1-[4-(2-propylbenzo[b]thiophen-5-yl)-3,6-dihydro-2H-pyridin-1-yl]ethanone;

Compound 69: Methyl 6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinate;

Compound 70: Methyl 6-{3-[2-(4-benzo[b]thiophen-5-yl-3,6-dihydro-2H-pyridin-1-yl)-2-oxoethyl]-3,8-diazabicyclo[3.2.1]oct-8-yl}nicotinate;

Compound 71: 6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinic acid;

Compound 72: 2-[(2S,6R)-2,6-dimethyl-4-(5-trifluoromethylpyridin-2-yl)piperazin-1-yl]-1-[4-(7-fluorobenzofuran-5-yl)-3,6-dihydro-2H-pyridin-1-yl]ethanone;

Compound 73: 1-[4-(2,3-dimethylbenzofuran-6-yl)-3,6-dihydro-2H-pyridin-1-yl]-2-[(2S,6R)-2,6-dimethyl-4-(5-trifluoromethylpyridin-2-yl)piperazin-1-yl]ethanone;

Compound 74: 2-[(2S,6R)-2,6-dimethyl-4-(5-trifluoromethylpyridin-2-yl)piperazin-1-yl]-1-(4-quinolin-2-yl-3,6-dihydro-2H-pyridin-1-yl)ethanone;

Compound 75: 1-(4-benzofuran-5-yl-3,6-dihydro-2H-pyridin-1-yl)-2-(2,3,5,6-tetrahydro-[1,2']bipyrazinyl-4-yl)ethanone;

Compound 76: Methyl 6-{3-[2-oxo-2-(4-thieno[3,2-c]pyridin-4-yl-3,6-dihydro-2H-pyridin-1-yl)ethyl]-3,8-diazabicyclo[3.2.1]oct-8-yl}nicotinate;

Compound 77: Methyl 6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinate;

Compound 78: 1-(4-benzofuran-7-yl-3,6-dihydro-2H-pyridin-1-yl)-2-(4-pyridin-3-yl-[1,4]diazepan-1-yl)ethanone;

Compound 79: 6-{3-[2-oxo-2-(4-thieno[3,2-c]pyridin-4-yl-3,6-dihydro-2H-pyridin-1-yl)ethyl]-3,8-diazabicyclo[3.2.1]oct-8-yl}nicotinic acid;

Compound 80: 6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinic acid;

Compound 81: Methyl 6-{3-[2-(3-benzofuran-7-yl-2,5-dihydropyrrol-1-yl)-2-oxoethyl]-3,8-diazabicyclo[3.2.1]oct-8-yl}nicotinate;

Compound 82: Methyl 6-{3-[2-(3-benzo[b]thiophen-7-yl-2,5-dihydropyrrol-1-yl)-2-oxoethyl]-3,8-diazabicyclo[3.2.1]oct-8-yl}nicotinate;

Compound 83: 4-[2-(3-benzofuran-7-yl-2,5-dihydropyrrol-1-yl)-2-oxoethyl]-1-(5-trifluoromethylpyridin-2-yl)piperazin-2-one;

Compound 84: 6-{3-[2-(3-benzofuran-7-yl-2,5-dihydropyrrol-1-yl)-2-oxoethyl]-3,8-diazabicyclo[3.2.1]oct-8-yl}nicotinic acid;

Compound 85: 6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinic acid;

Compound 86: 6-{3-[2-(3-benzo[b]thiophen-7-yl-2,5-dihydropyrrol-1-yl)-2-oxoethyl]-3,8-diazabicyclo[3.2.1]oct-8-yl}nicotinic acid;

Compound 87: Methyl 6-(3-{2-[4-(2,3-dihydrobenzo[1,4]dioxin-6-yl)-3,6-dihydro-2H-pyridin-1-yl]-2-oxoethyl}-3,8-diazabicyclo[3.2.1]oct-8-yl)nicotinate;

Compound 88: 2-{(3S,5R)-4-[2-(4-benzo[b]thiophen-7-yl-3,6-dihydro-2H-pyridin-1-yl)-2-oxoethyl]-3,5-dimethylpiperazin-1-yl}pyrimidine-5-carboxylic acid;

Compound 89: 3-(6-{3-[2-(4-benzofuran-7-yl-3,6-dihydro-2H-pyridin-1-yl)-2-oxoethyl]-3,8-diazabicyclo[3.2.1]oct-8-yl}pyridin-3-yl)-4H-[1,2,4]oxadiazol-5-one;

Compound 90: 3-(6-{3-[2-(4-benzo[b]thiophen-7-yl-3,6-dihydro-2H-pyridin-1-yl)-2-oxoethyl]-3,8-diazabicyclo[3.2.1]oct-8-yl}pyridin-3-yl)-4H-[1,2,4]oxadiazol-5-one;

Compound 91: 6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinonitrile;

Compound 92: 1-(4-benzofuran-7-yl-3,6-dihydro-2H-pyridin-1-yl)-2-[(2S,6R)-4-(3-chloro-5-trifluoromethylpyridin-2-yl)-2,6-dimethylpiperazin-1-yl]ethanone;

Compound 93: 1-(4-benzofuran-7-yl-3,6-dihydro-2H-pyridin-1-yl)-2-(8-pyridin-3-yl-3,8-diazabicyclo[3.2.1]oct-3-yl)ethanone;

Compound 94: 6-{3-[2-(4-benzofuran-7-yl-3,6-dihydro-2H-pyridin-1-yl)-2-oxoethyl]-3,8-diazabicyclo[3.2.1]oct-8-yl}nicotinonitrile;

Compound 95: 1-(4-benzofuran-7-yl-3,6-dihydro-2H-pyridin-1-yl)-2-[5-(5-trifluoromethylpyridin-2-yl)-2,5-diazabicyclo[2.2.1]hept-2-yl]ethanone;

Compound 96: cyclobutyl 6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinate;

Compound 97: 2-[(2S,6R)-2,6-dimethyl-4-(5-trifluoromethylpyridin-2-yl)piperazin-1-yl]-1-[4-(1H-indol-3-yl)-3,6-dihydro-2H-pyridin-1-yl]ethanone;

Compound 98: 1-[4-(1H-indol-3-yl)-3,6-dihydro-2H-pyridin-1-yl]-2-(4-quinolin-2-ylpiperazin-1-yl)ethanone;

Compound 99: 1-(4-benzofuran-7-yl-3,6-dihydro-2H-pyridin-1-yl)-2-[4-(7-chloroquinolin-4-yl)piperazin-1-yl]ethanone;

Compound 100: 2-[(2S,6R)-4-(5-fluoropyrimidin-2-yl)-2,6-dimethylpiperazin-1-yl]-1-[4-(1H-indol-3-yl)-3,6-dihydro-2H-pyridin-1-yl]ethanone;

Compound 101: 1-(4-benzo[b]thiophen-7-yl-3,6-dihydro-2H-pyridin-1-yl)-2-[(2S,6R)-4-(5-chloropyridin-2-yl)-2,6-dimethylpiperazin-1-yl]ethanone;

Compound 102: 1-(4-benzo[b]thiophen-7-yl-3,6-dihydro-2H-pyridin-1-yl)-2-((2R,5S)-2,5-dimethyl-4-pyrimidin-2-yl-piperazin-1-yl)ethanone;

Compound 103: 1-(4-benzo[b]thiophen-7-yl-3,6-dihydro-2H-pyridin-1-yl)-2-[8-(5-fluoropyrimidin-2-yl)-3,8-diazabicyclo[3.2.1]oct-3-yl]ethanone;

Compound 104: 1-(4-benzo[b]thiophen-7-yl-3,6-dihydro-2H-pyridin-1-yl)-2-[8-(6-trifluoromethylpyridin-2-yl)-3,8-diazabicyclo[3.2.1]oct-3-yl]ethanone;

Compound 105: 1-(4-benzo[b]thiophen-7-yl-3,6-dihydro-2H-pyridin-1-yl)-2-(4-quinolin-2-ylpiperazin-1-yl)ethanone;

Compound 106: 1-(4-benzo[b]thiophen-7-yl-3,6-dihydro-2H-pyridin-1-yl)-2-[4-(7-chloroquinolin-4-yl)piperazin-1-yl]ethanone;

Compound 107: 1-(4-benzo[b]thiophen-7-yl-3,6-dihydro-2H-pyridin-1-yl)-2-[4-(6-chloropyridin-2-yl)piperazin-1-yl]ethanone;

Compound 108: 2-[4-(6-chloropyridin-2-yl)piperazin-1-yl]-1-[4-(1H-indol-3-yl)-3,6-dihydro-2H-pyridin-1-yl]ethanone;

Compound 109: 1-[4-(1H-indol-3-yl)-3,6-dihydro-2H-pyridin-1-yl]-2-[4-(5-trifluoromethylpyridin-2-yl)piperazin-1-yl]ethanone;

Compound 110: 2-((2S,6R)-2,6-dimethyl-4-quinolin-2-yl-piperazin-1-yl)-1-[4-(1H-indol-3-yl)-3,6-dihydro-2H-pyridin-1-yl]ethanone;

Compound 111: 1-(4-benzo[b]thiophen-7-yl-3,6-dihydro-2H-pyridin-1-yl)-2-(4-pyridin-3-yl-[1,4]diazepan-1-yl)ethanone;

Compound 112: 1-(4-benzo[b]thiophen-7-yl-3,6-dihydro-2H-pyridin-1-yl)-2-[4-(5,6-dichloropyridin-2-yl)piperazin-1-yl]ethanone;

Compound 113: 1-(4-benzo[b]thiophen-7-yl-3,6-dihydro-2H-pyridin-1-yl)-2-[4-(6-bromopyridin-2-yl)piperazin-1-yl]ethanone;

Compound 114: 1-[4-(2-methylbenzo[b]thiophen-5-yl)-3,6-dihydro-2H-pyridin-1-yl]-2-(4-quinolin-2-ylpiperazin-1-yl)ethanone;

Compound 115: 1-(4-benzo[b]thiophen-7-yl-3,6-dihydro-2H-pyridin-1-yl)-2-[5-(6-trifluoromethylpyridazin-3-yl)-2,5-diazabicyclo[2.2.1]hept-2-yl]ethanone;

Compound 116: 1-[4-(2-methylbenzo[b]thiophen-5-yl)-3,6-dihydro-2H-pyridin-1-yl]-2-[4-(6-trifluoromethylpyridin-2-yl)piperazin-1-yl]ethanone;

Compound 117: 2-[4-(7-chloroquinolin-4-yl)piperazin-1-yl]-1-[4-(2-methylbenzo[b]thiophen-5-yl)-3,6-dihydro-2H-pyridin-1-yl]ethanone;

Compound 118: 4-[2-oxo-2-(4-thieno[3,2-c]pyridin-4-yl-3,6-dihydro-2H-pyridin-1-yl)ethyl]-1-(5-trifluoromethylpyridin-2-yl)piperazin-2-one;

Compound 119: 1-(4-benzofuran-7-yl-3,6-dihydro-2H-pyridin-1-yl)-2-[(2S,6R)-2,6-dimethyl-4-(5-thiazol-2-ylpyridin-2-yl)piperazin-1-yl]ethanone;

Compound 120: 1-(4-benzofuran-7-yl-3,6-dihydro-2H-pyridin-1-yl)-2-{(2S,6R)-2,6-dimethyl-4-[5-(2-methyl-2H-tetrazol-5-yl)pyridin-2-yl]piperazin-1-yl}ethanone;

Compound 121: 2-[(2S,6R)-2,6-dimethyl-4-(5-trifluoromethylpyridin-2-yl)piperazin-1-yl]-1-(4-quinolin-2-yl-3,6-dihydro-2H-pyridin-1-yl)ethanone;

Compound 122: 4-[2-oxo-2-(4-quinolin-2-yl-3,6-dihydro-2H-pyridin-1-yl)ethyl]-1-(5-trifluoromethylpyridin-2-yl)piperazin-2-one;

Compound 123: 1-(4-quinolin-2-yl-3,6-dihydro-2H-pyridin-1-yl)-2-[8-(5-trifluoromethylpyridin-2-yl)-3,8-diazabicyclo[3.2.1]oct-3-yl]ethanone;

Compound 124: 1-(4-benzofuran-7-yl-3,6-dihydro-2H-pyridin-1-yl)-2-{8-[5-(1-methyl-1H-tetrazol-5-yl)pyridin-2-yl]-3,8-diazabicyclo[3.2.1]oct-3-yl}ethanone;

Compound 125: 1-(4-benzofuran-7-yl-3,6-dihydro-2H-pyridin-1-yl)-2-[(2S,6R)-4-(5-methanesulfonylpyridin-2-yl)-2,6-dimethylpiperazin-1-yl]ethanone;

in the form of a base or of an acid-addition salt.

In the text hereinbelow, the term "protecting group Pg" mean a group that makes it possible, firstly, to protect a reactive function such as a hydroxyl or an amine during a synthesis, and, secondly, to regenerate the intact reactive function at the end of the synthesis. Examples of protecting groups and of protection and deprotection methods are given in *Protective Groups in Organic Synthesis*, Green et al., 2$^{nd}$ Edition (John Wiley & Sons, Inc., New York).

In accordance with the invention, the compounds of general formula (I) may be prepared according to the process that follows.

Scheme 1

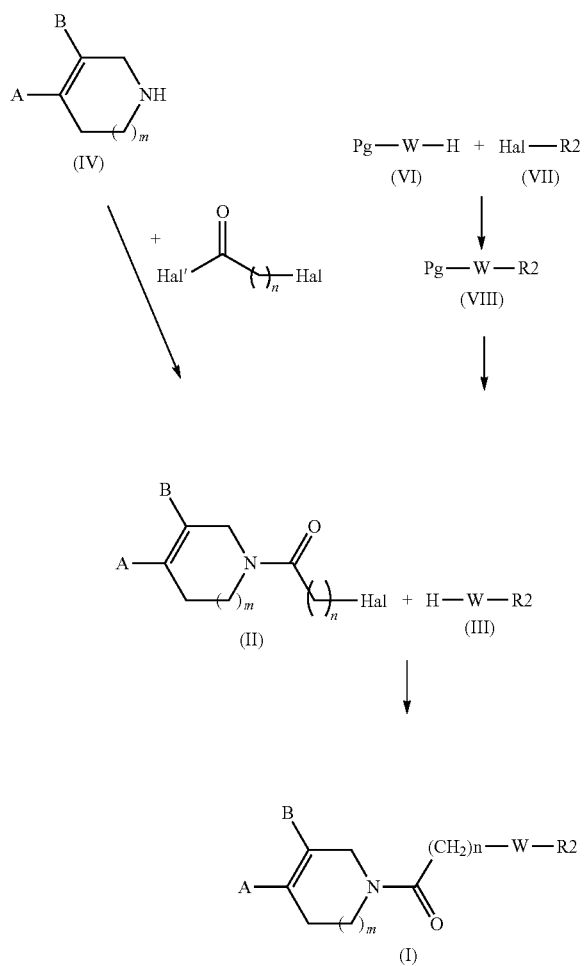

More specifically, the process for preparing the compounds of general formula (I) in which A, B, m, n, W and R2 are as defined previously comprises the reaction of a compound of formula (II):

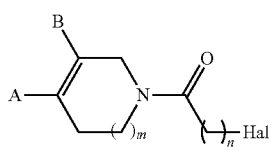

in which A, B, m and n are defined as in the general formula (I) and Hal represents a halogen atom, for example chlorine, and of a compound of general formula (III):

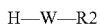 (III)

in which W and R2 are defined as in the general formula (I), according to methods known to those skilled in the art, for example in the presence of a base, in a solvent as described in WO 03/104225. Thus, bases that may be mentioned include organic bases such as triethylamine, N,N-diisopropylamine, diisopropylethylamine (DPEA) or N-methylmorpholine or alkali metal carbonates or bicarbonates such as potassium carbonate, sodium carbonate or sodium bicarbonate and in the absence or presence of an alkali metal iodide such as potassium iodide or sodium iodide. The reaction is performed in a solvent such as acetonitrile, N,N-dimethylformamide (DMF), N-methylpyrrolidinone, toluene or 2-propanol, and at a temperature between room temperature and the reflux temperature of the solvent. The term "room temperature" means a temperature of between 5 and 25° C. By way of example, the reaction may be performed in the presence of sodium bicarbonate, sodium iodide in a solvent such as DMF. These reactions may also be performed in a microwave reactor.

In the products of general formula (I) thus obtained, R, R1, R3, R4, R5 and R6 may be modified via treatments commonly used by those skilled in the art, for instance hydrolysis of an ester group to give a carboxylic group or of a cyano to obtain a tetrazole group.

Generally, the acid-addition salts of the compounds of general formula (I) may be obtained by adding the appropriate acid, such as hydrochloric acid, hydrobromic acid or oxalic acid.

The compounds of formula (III), optionally in the form of salts, may be prepared from the corresponding compounds of formula (VIII):

Pg—W—R2    (VIII)

in which W and R2 are as defined in formula (I) and Pg represents a protecting group for a nitrogen atom of W. Preferably, Pg is a benzyl group and the deprotection is performed according to standard methods that are well known to those skilled in the art, for example via catalytic hydrogenation over Pd/C or by treatment with chloroformates followed by hydrolysis in acidic medium.

The compounds of formula (VIII) may be prepared from the compounds of formula (VI):

Pg—W—H    (VI)

and (VII):

Hal-R2    (VII)

in which Pg, W and R2 are defined as previously and Hal represents a halogen atom, preferably chlorine. This reaction is generally performed under the same conditions as the reaction for the preparation of the compounds of formula (I) from the compounds of formulae (II) and (III).

Alternatively, the compounds of formula (VIII) may be prepared via the Buchwald coupling method in the presence of a suitably selected palladium catalyst and a suitably selected phosphine, using as solvent inert solvents such as toluene or xylene, at a temperature between room temperature and 110° C.

In the compounds of general formula (VIII) thus obtained, R7 and R8 may be modified via treatments commonly used by those skilled in the art, for instance the synthesis of an oxadiazole group starting with a cyano group or via the formation of a boronic intermediate and via Suzuki coupling as described in the scheme below.

Scheme 2

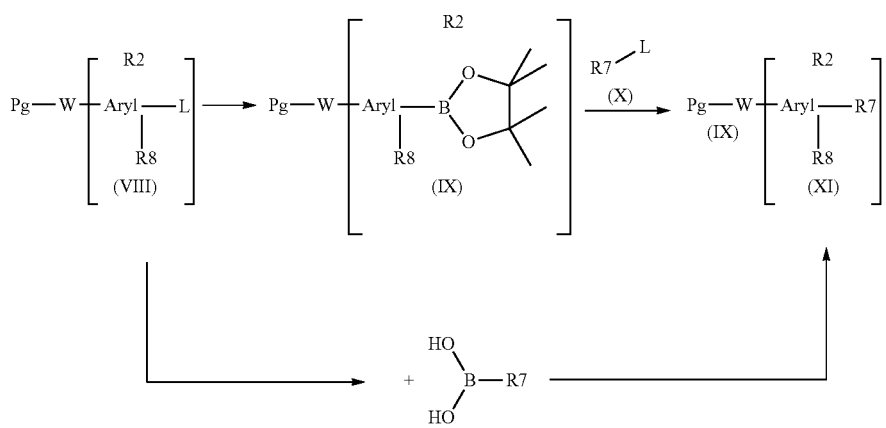

In Scheme 2 above, L represents a leaving group such as iodo, bromo or trifluoromethanesulfonate, R7 represents heterocycles as described in the general formula (I), R8 is as defined in the general formula (I) and B is a boron atom.

Examples of such reactions are described in the experimental section.

The compounds of formula (III), optionally in the form of salts, when W represents an oxopiperazine, are commercially available or described in the literature, or may be prepared from the corresponding compounds of formula (VIII) according to methods that are described or known to those skilled in the art.

Examples of such preparations are described in the experimental section.

The compounds of formula (II) may be obtained by reacting a corresponding compound of formula (IV):

in which A, B and m are defined as in the general formula (I), optionally in the form of an acid-addition salt, with a compound of formula (V):

in which Hal and n are as defined in formula (II) and Hal' represents a halogen atom, which may be identical to or different than Hal. Preferably, Hal' represents a chlorine atom.

This reaction is generally performed in the presence of a base such as triethylamine, N,N-diisopropylethylamine or N-methylmorpholine, in a solvent such as dichloromethane, chloroform, tetrahydrofuran, dioxane or a mixture of these solvents, and at a temperature of between 0° C. and room temperature. The compounds of formula (V) are generally commercially available.

Optionally, the process according to the invention comprises the subsequent step that consists in isolating the desired product obtained.

The products of formulae (IV), (V), (VI) and (VII) and the reactants, when their preparation method is not described, are commercially available or described in the literature, or else may be prepared according to methods that are described or known to those skilled in the art.

Alternatively, the compounds of formula (I) may be prepared according to the following process:

Scheme 3

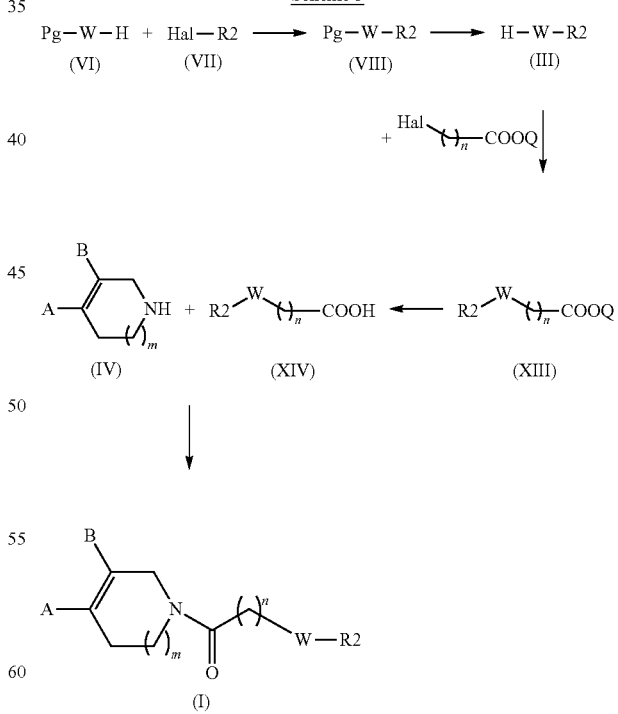

More specifically, the process for preparing the compounds of general formula (I) in which A, B, R2, m and n are as defined previously comprises the reaction of a compound of formula (XIV):

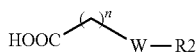

(XIV)

in which R2, W and n are defined as in the general formula (I) and of a compound of general formula (IV)

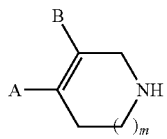

(IV)

in which A, B and m are defined as in the general formula (I), according to methods known to those skilled in the art, for example in a solvent such as dichloromethane, DMF or THF, in the presence of a base such as pyridine, triethylamine, N,N-diisopropylamine or diisopropylethylamine (DPEA) and of a coupling agent such as BOP, DBU or DCC. The reaction is performed at a temperature between room temperature and the reflux temperature of the solvent. The term "room temperature" means a temperature between 5 and 25° C. By way of example, the reaction may be performed in the presence of sodium bicarbonate, sodium iodide in a solvent such as DMF. These reactions may also be performed in a microwave reactor.

In the compounds of general formula (I) thus obtained, R, R1, R3, R4, R5, R6, R7 and R8 may be modified with treatments commonly used by those skilled in the art, for instance by hydrolysis of an ester group to give a carboxylic group or of a cyano to obtain a tetrazole group.

Generally, the acid-addition salts of the compounds of general formula (I) may be obtained by adding the appropriate acid, such as hydrochloric acid, hydrobromic acid or oxalic acid.

The compounds of formula (XIV) may be obtained from compounds of formula (XIII)

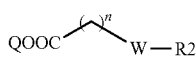

(XIII)

in which R2, W and n are defined as in the general formula (I) and Q represents a residue that is capable of forming an ester, such as methyl, ethyl or benzyl, by hydrolysis of the ester bond, according to methods that are well known to those skilled in the art, for example via a treatment in an acidic or basic aqueous medium, or alternatively via reduction in a polar solvent such as an alcohol or THF, under a stream of hydrogen.

The compounds of formula (XIII) may be obtained from compounds of formula (III)

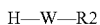

(III)

in which R2 and W are defined as in the general formula (I), optionally in the form of an acid-addition salt, and from a compound of formula (XII):

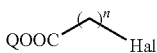

(XII)

in which Q represents a residue that is capable of forming an ester, such as methyl, ethyl or benzyl, Hal represents a halogen atom, preferably a chlorine atom, and n is as defined in the general formula (I).

This reaction is generally performed in the presence of a base, such as triethylamine, N,N-diisopropylethylamine or N-methylmorpholine, in a solvent such as dichloromethane, chloroform, tetrahydrofuran, dioxane or a mixture of these solvents, and at a temperature between 0° C. and room temperature. The compounds of formula (XII) are generally commercially available.

The compounds of formula (III), optionally in the form of salts, may be prepared from the corresponding compounds of formula (VIII):

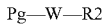

(VIII)

in which W and R2 are as defined in formula (I) and Pg represents a protecting group for a nitrogen atom of W. Preferably, Pg is a benzyl group and the deprotection is performed according to standard methods that are known to those skilled in the art, for example via catalytic hydrogenation over Pd/C or by treatment with chloroformates followed by hydrolysis in acidic medium.

The compounds of formula (VIII) may be prepared from the compounds of formula (VI):

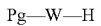

(VI)

and (VII):

(VII)

in which Pg, W and R2 are defined as previously and Hal represents a halogen atom, preferably chlorine. This reaction is generally performed under the same conditions as the reaction for preparing the compounds of formula (I) from the compounds of formulae (II) and (III).

Alternatively, the compounds of formula (VIII) may be prepared via the Buchwald coupling method in the presence of a suitably selected palladium catalyst and a suitably selected phosphine, using as solvent inert solvents such as toluene or xylene, at a temperature of between room temperature and 110° C. In the compounds of general formula (VIII) thus obtained, R7 and R8 may be modified via treatments generally used by those skilled in the art, for instance the synthesis of an oxadiazole group starting with a cyano group, or alternatively via Suzuki couplings as already described in Scheme 2 presented hereinabove.

The compounds of formula (III), optionally in the form of salts, where W represents an oxopiperazine, are commercially available or described in the literature, or else may be prepared, from the corresponding compounds of formula (VII), according to methods that are described or known to those skilled in the art.

Examples of such preparations are described in the experimental section.

Optionally, the process according to the invention comprises the subsequent step that consists in isolating the desired product obtained.

The products of formulae (IV), (VI), (VII) and (XII) and the reactants, when their preparation method is not described, are commercially available or described in the literature, or else may be prepared according to methods that are described or known to those skilled in the art.

Examples of such preparations are described in the experimental section.

According to another of its aspects, a subject of the invention is also compounds of formula (II)

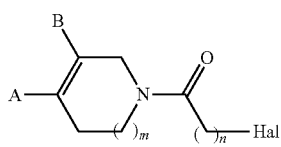

in which A, B, n and m are defined as in the general formula (I) and Hal represents a halogen atom, preferably chlorine; optionally in the form of an acid-addition salt. These compounds are useful as intermediates in the synthesis of the compounds of formula (I).

The examples that follow describe the preparation of certain compounds in accordance with the invention. These examples are not limiting, and serve merely to illustrate the present invention. The numbers of the compounds presented as examples refer to those given in the table hereinbelow, which illustrates the chemical structures and physical properties of a number of compounds according to the invention.

The physicochemical measurements were performed in the following manner:

The melting points were measured using a Buchi B540 machine.

The proton nuclear magnetic resonance (1H NMR) spectra were recorded under the following conditions:

a) at 500 MHz on a Bruker machine equipped with an Avance III console;

b) at 400 MHz on a Bruker machine equipped with an Avance I console.

The chemical shifts are reported in ppm relative to the TMS frequency.

The spectra were recorded under the following temperature conditions:

Temp. A: 40° C.

Temp. B: 30° C.

The abbreviations used to characterize the signals are the following: s=singlet, bs=broad singlet, m=multiplet, bm=broad multiplet, d=doublet, bd=broad doublet, t=triplet, q=quadruplet.

*=not integratable because of the interference with a broad peak due to water.

**=not integratable because of the interference with a peak due to the NMR solvent.

2×s=two partially superposed singlets.

2×bs=two partially superposed broad singlets.

2×m=two partially superposed multiplets.

The compounds are analyzed by HPLC-UV-MS (liquid chromatography-UV detection and mass detection) coupling.

The machine used is composed of a Thermo Surveyor chromatographic line equipped with a Thermo diode array detector and a Thermo Deca XPMax ion-trap mass spectrometer.

The analytical conditions are as follows:

HPLC Conditions

Various HPLC conditions were used according to the compounds:

Method A

Eluent A: $H_2O$+TFA 0.005%+$CH_3CN$ 5%

Eluent B: $CH_3CN$

Gradient:

| Time (min) | % B |
| --- | --- |
| 0 | 5 |
| 17 | 90 |
| 22 | 90 |
| 23 | 5 |
| 30 | 5 |

Column temperature: 30° C.

Flow rate: 0.3 ml/min

Detection: $\lambda$=220 nm

Method B

Eluent A: $H_2O$+TFA 0.005%

Eluent B: $CH_3CN$

Gradient:

| Time (min) | % B |
| --- | --- |
| 0 | 5 |
| 22 | 90 |
| 29 | 90 |
| 30 | 5 |
| 40 | 5 |

Column temperature: not controlled

Flow rate: 0.3 ml/min

Detection: $\lambda$=220 nm

Method C

Eluent A: $AcONH_4$ 5 mM at pH 6.5

Eluent B: $CH_3CN$

Gradient:

| Time (min) | % B |
| --- | --- |
| 0 | 5 |
| 25 | 90 |
| 30 | 90 |
| 32 | 5 |
| 40 | 5 |

Column temperature: not controlled

Flow rate: 0.3 ml/min

Detection: $\lambda$=220 nm

Method D

Eluent A: $AcONH_4$ 5 mM at pH 6.5

Eluent B: $CH_3CN$

Gradient:

| Time (min) | % B |
| --- | --- |
| 0 | 5 |
| 17 | 90 |
| 22 | 90 |

-continued

| Time (min) | % B |
|---|---|
| 23 | 5 |
| 30 | 5 |

Column temperature: not controlled
Flow rate: 0.3 ml/min
Detection: $\lambda$=220 nm
  Method E
Eluent A: $H_2O$+TFA 0.01%
Eluent B: $CH_3CN$
Gradient:

| Time (min) | % B |
|---|---|
| 0 | 10 |
| 18 | 95 |
| 20 | 95 |
| 21 | 10 |
| 25 | 10 |

Column temperature: 40° C.
Flow rate: 0.5 ml/min
Detection: $\lambda$=220 nm
  Method F
Eluent A: $H_2O$+TFA 0.005%
Eluent B: $CH_3CN$
Gradient:

| Time (min) | % B |
|---|---|
| 0 | 10 |
| 18 | 60 |
| 20 | 60 |
| 21 | 10 |
| 25 | 10 |

Column temperature: not controlled
Flow rate: 0.3 ml/min
Detection: $\lambda$=220 nm
  Method G
Eluent A: $AcONH_4$ 5 mM at pH 6.5
Eluent B: $CH_3CN$
Gradient:

| Time (min) | % B |
|---|---|
| 0 | 40 |
| 25 | 40 |

Column temperature: not controlled
Flow rate: 0.3 ml/min
Detection: $\lambda$=220 nm
  Method H
Eluent A: $H_2O$+TFA 0.05%
Eluent B: $CH_3CN$+TFA 0.035%
Gradient:

| Time (min) | % B |
|---|---|
| 0 | 10 |
| 22 | 90 |
| 29 | 90 |

-continued

| Time (min) | % B |
|---|---|
| 30 | 10 |
| 40 | 10 |

Column temperature: 40° C.
Flow rate: 0.3 ml/min
Detection: $\lambda$=220 nm
  Method I
Eluent A: $H_2O$+TFA 0.01%
Eluent B: $CH_3CN$
Gradient:

| Time (min) | % B |
|---|---|
| 0 | 2 |
| 10 | 95 |
| 15 | 95 |
| 16 | 2 |
| 20 | 2 |

Column temperature: 40° C.
Flow rate: 0.5 ml/min
Detection: $\lambda$=220 nm
The columns used are C18 columns with a particle size of between 2 and 5 μm, preferably 3.5 μm.

Mass Spectrometry Conditions

The mass spectra are recorded in positive or negative electrospray (ESI) mode, in order to observe the ions derived from the protonation of the analyzed compounds ($MH^+$ or $MH^-$), or the formation of adducts with other cations such as $Na^+$, $K^+$, etc.

Thin-layer chromatography was performed on Merck Silica Gel 60 silica gel TLC plates. The silica gel for the flash column chromatography is sold by Biotage or Supelco.

All the solvents used are of "reagent grade" or "HPLC grade" purity.

Preparation 1

(3R,5S)-3,5-dimethyl-1-(5-trifluoromethylpyridin-2-yl)piperazine 0.8 g of 2-chloro-5-(trifluoromethyl)pyridine (compound of formula (VII)), 0.5 g of cis-2,6-dimethylpiperazine (compound of formula (VI)), 0.67 g of potassium carbonate and 0.3 g of NaI are placed in 8 ml of DMF. The reaction is performed in a CEMdiscover microwave initiator for 30 minutes at 160° C. The mixture is then poured into saturated aqueous sodium chloride solution and extracted with ethyl acetate. The organic phase is dried over $Na_2SO_4$, filtered and evaporated under vacuum. 1.1 g of an oily material corresponding to the title product are isolated.

Preparation 2

(3R,5S)-2,5-dimethyl-1-(5-trifluoromethylpyridin-2-yl)piperazine

By performing the process as described in Preparation 1, but using 2,5-trans-dimethylpiperazine instead of cis-2,6-dimethylpiperazine, the title compound is obtained in the form of an oily material.

Preparation 3

8-(5-fluoropyrimidin-2-yl)-3,8-diazabicyclo[3.2.1]octane hydrochloride 1.44 g of 2-chloro-5-fluoropyrimidine (compound of formula (VII)), 2.2 g of 3-benzyl-3,8-diazabicyclo[3.2.1]octane (compound of formula (VI)), 1.7 g of potassium carbonate and 0.73 g of NaI are placed in 27 ml of N-methylpyrrolidone. The mixture is heated at 110° C. for 5 hours. It is then poured into saturated aqueous sodium chloride solution and extracted with ethyl acetate. The organic phase is dried over $Na_2SO_4$, filtered and evaporated under vacuum. 3.2 g of an oily material are isolated, and this material is purified by flash chromatography on a Biotage® column, using 95/5 cyclohexane/ethyl acetate as eluent. 1.4 g of a white solid are isolated, and are dissolved in 35 ml of 1,2-dichloroethane. 0.72 ml of 1-chloroethyl chloroformate is added at 0° C. and the mixture is stirred under a stream of nitrogen for 10 minutes at 0° C. and then for 3 hours at 85° C. The solvent is evaporated off and 35 ml of methanol are added. The mixture is heated for 30 minutes at the reflux temperature. The solvent is evaporated off and the residue is treated with isopropanol. A white solid is obtained, which is filtered off, and 900 mg of title product are isolated. m.p.=236-239° C.

Preparation 4

(3R,5S)-3,5-dimethyl-1-(6-trifluoromethylpyridin-3-yl)piperazine 2.2 g of 2-trifluoromethyl-5-bromopyridine (compound of formula (VII)), 1.1 g of cis-2,6-dimethylpiperazine (compound of formula (VI)), 0.22 g of palladium acetate, 0.28 g of sodium t-butoxide and 1.3 g of tri-t-butylphosphine are placed in 16 ml of o-xylene. The mixture is heated at 120° C. for 6 hours. The resulting mixture is filtered through celite and the solvent is evaporated off. 1.8 g of an oily material corresponding to the title product are isolated.

Preparation 5

Methyl 6-(3,8-diazabicyclo[3.2.1]oct-8-yl)nicotinate hydrochloride 0.42 g of methyl 6-chloronicotinate (compound of formula (VII)), 0.5 g of 3-benzyl-3,8-diazabicyclo[3.2.1]octane (compound of formula (VI)), 0.4 g of potassium carbonate and 0.17 g of NaI are placed in 7 ml of N-methylpyrrolidone. The mixture is heated for 7 hours at 110° C. It is then poured into saturated aqueous sodium chloride solution and extracted with ethyl acetate. The organic phase is dried over $Na_2SO_4$, filtered and evaporated under vacuum. 1.1 g of an oily material are isolated, and this material is purified by flash chromatography on a Biotage® column, using 8/2 cyclohexane/ethyl acetate as eluent. 520 mg of a clear oil are isolated. The product obtained in the preceding step is hydrogenated at 40° C. under atmospheric pressure for 2 hours, in 20 ml of ethanol and 2 ml of isopropanol/HCl, in the presence of 0.22 g of 10% Pd/C. The resulting mixture is filtered and evaporated under vacuum, and 440 mg of the title product are isolated in the form of a white solid corresponding to the title product.

Preparation 6

1-(5-trifluoromethylpyridin-2-yl)piperazin-2-one hydrochloride 10 g of 2-chloro-5-(trifluoromethyl)pyridine and 40.5 ml of N-benzylethylenediamine are heated at 135° C. for 6 hours in a round-bottomed flask. The resulting mixture is poured into water and extracted with ethyl acetate. The extracts are dried and evaporated under vacuum; the crude product thus obtained is purified by flash chromatography. The isolated product (compound of formula (VIII)), 14 g, is dissolved in 200 ml of 2N HCl solution. 30 g of trimeric glyoxal dihydrate are added and the mixture is stirred at room temperature for 72 hours. The resulting mixture is extracted with ethyl acetate. The extracts are dried and evaporated under vacuum; the crude product thus obtained is purified by flash chromatography. The isolated product, 10 g, is dissolved in 450 ml of ethanol, followed by addition of 15 ml of a solution of isopropanol saturated with HCl and 3 g of 10% Pd/C. This mixture is reacted under a stream of hydrogen for 4 hours at a temperature of 40° C. The resulting mixture is filtered and evaporated under vacuum to give 3 g of the title compound, m.p.=205-207° C.

Preparation 7

2-chloro-1-4-benzo[b]thiophen-7-yl-3,6-dihydro-2H-pyridin-1-yl)ethanone

Step a) preparation of 1-(t-butoxycarbonyl)-4-(7-benzo[b]thiophene)-4-hydroxypiperidine 45 g of 7-bromobenzothiophene are dissolved in 135 ml of THF and the solution thus obtained is added dropwise to a suspension of 5.13 g of magnesium in 10 ml of THF in a round-bottomed flask under nitrogen. A catalytic amount of iodine is added and the mixture is heated at the reflux temperature for 3 hours. The resulting mixture is cooled to room temperature and a solution of 36 g of 1-(t-butoxycarbonyl)-4-piperidone in 80 ml of THF is added. This mixture is stirred for 3 hours at room temperature, and saturated ammonium chloride solution is added.

The resulting mixture is extracted with ethyl acetate. The extracts are dried and evaporated under vacuum; the crude product thus obtained is purified by flash chromatography using 95/5 hexane/ethyl acetate as eluent. 47.5 g of a white solid with a melting point of 130-131° C. are isolated.

Step b) preparation of 4-(7-benzo[b]thiophene)-4-hydroxypiperidine hydrochloride 40 g of the product from step a) are dissolved in 650 ml of ethyl acetate. 88 ml of 37% HCl are added slowly and the mixture is stirred at room temperature for 30 minutes. The solvents are evaporated off and the residue is treated with acetone. The resulting mixture is filtered to give 34 g of a white solid with a melting point of 232-233° C.

Step c) preparation of 4-(7-benzo[b]thiophene)-1,2,3,6-tetrahydropyridine hydrochloride 34 g of the product from step b) are dissolved in 437 ml of acetic acid.

20 ml of 96% sulfuric acid are added and the mixture is heated at a temperature of 60° C. for 2 hours. The resulting mixture is poured into a water/ice mixture and the pH is made basic with 40% sodium hydroxide solution. The resulting mixture is extracted with ethyl acetate. The extracts are dried and evaporated under vacuum to give 30 g of product in the form of an oily material. The formation of the hydrochloride is obtained in isopropanol using a solution of isopropanol saturated with HCl. The product is filtered off to give 25.8 g of a white solid with a melting point of 226-227° C.

Step d) preparation of 2-chloro-1-4-benzo[b]thiophen-7-yl-3,6-dihydro-2H-pyridin-1-yl)ethanone 2.8 g of the product from step c) are suspended in 50 ml of dichloromethane in a round-bottomed flask equipped with a magnetic stirrer. 2.8 ml of triethylamine are added and the mixture is cooled to 0° C. At 0° C., 1.5 ml of chloroacetyl chloride, i.e. the compound of general formula (V) in which Hal=Hal'=Cl and n=1, are added dropwise. The mixture is reacted for 1 hour 30 minutes and is poured into water. The resulting mixture is extracted with dichloromethane. The organic phase is dried over $Na_2SO_4$, filtered and evaporated under vacuum. 4.1 g of an oil material are isolated, and this material is purified by flash chromatography on a Biotage® column, using 9/1 cyclohexane/ethyl acetate as eluent. 1.1 mg of the title product are isolated in the form of a clear oil.

Preparation 8

1-(4-benzofuran-7-yl-3,6-dihydro-2H-pyridin-1-yl)-2-chloroethanone

By performing the process as described in Preparation 7, but using 7-bromobenzofuran instead of 7-bromobenzothiophene, the title compound is obtained.

Preparation 9

1-(5-benzofuran-7-yl-3,6-dihydro-2H-pyridin-1-yl)-2-chloroethanone

By performing the process as described in Preparation 7, but using 7-bromobenzofuran instead of 7-bromobenzothiophene and 1-(t-butoxycarbonyl)-3-piperidone instead of 1-(t-butoxycarbonyl)-4-piperidone, the title compound is obtained.

Preparation 10

Methyl 5-[1-(2-chloroacetyl)-1,2,3,6-tetrahydropyridin-4-yl]-benzo[b]thiophene-2-carboxylate Step a) preparation of tert-Butyl 4-(2-methoxycarbonylbenzo[b]thiophen-5-yl)-3,6-dihydro-2H-pyridine-1-carboxylate 1.1 g of tert-butyl 4-(4,4,5,5-tetramethyl[1,3,2]dioxaborolan-2-yl)-3,6-dihydro-2H-pyridine-1-carboxylate (purity 70%), 0.7 g of methyl 5-bromobenzo[b]thiophene-2-carboxylate, 0.15 g of PalladiumTetrakis (PdP(Ph$_3$)$_4$), 5.5 ml of 2M sodium carbonate solution and 0.42 g of lithium chloride are placed in 30 ml of DME in a round-bottomed flask under a stream of nitrogen. The mixture is heated at the reflux temperature for 3 hours. The solvent is evaporated off and the residue is dissolved in 35 ml of ethyl acetate. This solution is washed with 2M sodium carbonate solution. The organic phase is dried over $Na_2SO_4$, filtered and evaporated under vacuum. 1.6 g of an oily material are isolated, and this material is purified by flash chromatography on a Biotage® column, using 98/2 cyclohexane/ethyl acetate as eluent. 0.45 g of a yellowish solid is isolated.

Step b) preparation of methyl 5-(1,2,3,6-tetrahydropyridin-4-yl)benzo[b]thiophene-2-carboxylate) hydrochloride 0.45 g of the product from step a) is dissolved in 25 ml of ethyl acetate. 50 ml of a solution of ethyl acetate saturated with HCl are added slowly and the mixture is stirred at room temperature for 3 hours. The solvents are evaporated off and the residue is treated with acetone. This mixture is filtered to give 0.35 g of a whitish solid.

Step c) preparation of methyl 5-[1-(2-chloroacetyl)-1,2,3,6-tetrahydropyridin-4-yl]benzo[b]thiophene-2-carboxylate By performing the process as described in step d) of Preparation 7, but using the product of step b) instead of the product of step c) of Preparation 7, 0.4 g of the title product is obtained in the form of a clear oil.

Preparation 11

2-chloro-1-(4-quinolin-8-yl-3,6-dihydro-2H-pyridin-1-yl)ethanone

By performing the process as described in Preparation 10, but using 8-bromoquinoline instead of methyl 5-bromobenzo[b]thiophene-2-carboxylate, the title compound is obtained.

Preparation 12

2-chloro-1-[4-(2,3-dihydrobenzo[1,4]dioxin-6-yl)-3,6-dihydro-2H-pyridin-1-yl]ethanone By performing the process as described in Preparation 7, but using 6-bromobenzodioxane instead of 7-bromobenzothiophene, the title compound is obtained.

Preparation 13

1-(3-benzofuran-7-yl-2,5-dihydropyrrol-1-yl)-2-chloroethanone

By performing the process as described in Preparation 7, but using 1-(t-butoxycarbonyl)-3-pyrrolidone instead of 1-(t-butoxycarbonyl)-4-piperidone and 7-bromobenzofuran instead of 7-bromobenzothiophene, the title compound is obtained.

Preparation 14

Methyl 6-((3S,5R)-3,5-dimethylpiperazin-1-yl)nicotinate

By performing the process as described in Preparation 1, but using methyl 6-chloronicotinate instead of 2-trifluoromethyl-5-bromopyridine, the title compound is obtained in the form of a clear oil.

Preparation 15

3-[6-(3,8-diazabicyclo[3.2.1]oct-8-yl)pyridin-3-yl]-4H-[1,2,4]oxadiazol-5-one hydrochloride

Step a) 6-(3,8-diazabicyclo[3.2.1]oct-8-yl)nicotinonitrile hydrochloride

By performing the process as described in Preparation 3, but using 6-chloronicotinonitrile instead of 2-chloro-5-fluoropyrimidine, the title compound is obtained in the form of a white solid.

Step b) tert-Butyl 8-(5-cyanopyridin-2-yl)-3,8-diazabicyclo[3.2.1]octane-3-carboxylate 7 g of the product from step a) are dissolved in 83 ml of DMF. 11.7 ml of triethylamine are added. 6.7 g of (BOC)$_2$O are added at 0° C., and the mixture is stirred at room temperature for 1 hour. The resulting mixture is evaporated under vacuum. The residue is washed with water and extracted with ethyl acetate. The organic phase is dried over Na$_2$SO$_4$, filtered and evaporated under vacuum. 12 g of an oily material are isolated, and this material is purified by flash chromatography on an automatic Biotage® column, using 8/2 cyclohexane/ethyl acetate in a gradient up to 100% ethyl acetate as eluent. 7.6 g of the title compound are isolated in the form of a white solid.

Step c) tert-Butyl 8-[5-(N-hydroxycarbamimidoyl)pyridin-2-yl]-3,8-diazabicyclo[3.2.1]octane-3-carboxylate The product of step b) (7.6 g) is dissolved in 75 ml of ethanol, and a solution of 3.36 g of hydroxylamine hydrochloride dissolved in 38 ml of water is added, followed by addition of 5 g of sodium carbonate. The mixture is stirred at 90° C. for 4 hours. The resulting mixture is cooled and filtered. 8 g of the title compound are obtained in the form of a white solid.

Step d) tert-Butyl 8-[5-(5-oxo-4,5-dihydro[1,2,4]oxadiazol-3-yl)pyridin-2-yl]-3,8-diazabicyclo[3.2.1]octane-3-carboxylate 1 g of the compound from step c) is placed in a round-bottomed flask under a stream of nitrogen, and 10 ml of DMF and 0.3 ml of pyridine are added. 0.23 ml of methyl chloroformate is added at 0° C., and the mixture is stirred at room temperature for 3 hours. The resulting mixture is washed with water and extracted with ethyl acetate. The organic phase is dried over Na$_2$SO$_4$, filtered and evaporated under vacuum. 30 ml of toluene are added and the resulting mixture is stirred at reflux for 4 hours. The solvent is evaporated off to give 0.8 g of the title compound.

Step e) 3-[6-(3,8-diazabicyclo[3.2.1]oct-8-yl)pyridin-3-yl]-4H-[1,2,4]oxadiazol-5-one hydrochloride The product is dissolved in 20 ml of ethyl acetate, a solution of ethyl acetate saturated with HCl is added, and the mixture is stirred at room temperature for 2 hours. The solvent is evaporated off and the residue is treated with isopropanol. This mixture is filtered to give 0.65 g of the title compound in the form of a yellow solid.

Preparation 16

[(2R,6S)-2,6-dimethyl-4-(5-trifluoromethylpyridin-2-yl)piperazin-1-yl]acetic acid

Step a) Ethyl [(2R,6S)-2,6-dimethyl-4-(5-trifluoromethylpyridin-2-yl)piperazin-1-yl]acetate 3.6 g of the product of Preparation 1, 100 ml of THF, 1.9 ml of ethyl bromoacetate and 4.7 ml of triethylamine are placed in a round-bottomed flask equipped with a magnetic stirrer. The mixture is reacted for 7 hours at 80° C. The solvent is evaporated off and the residue is washed with ethyl ether and filtered. The filtration water is purified by flash chromatography on an automatic Biotage® column using 8/2 cyclohexane/ethyl acetate at a gradient up to 7/3 ethyl acetate/methanol as eluent. 2.5 g of the title product are isolated in the form of a solid.

Step b) [(2R,6S)-2,6-dimethyl-4-(5-trifluoromethylpyridin-2-yl)piperazin-1-yl]acetic acid 2.5 g of the product from the preceding step are dissolved in 22 ml of ethanol, followed by addition of 5 ml of aqueous 40% NaOH solution. The mixture is reacted for 3 hours at 70° C. The pH is adjusted to 6 using 1N HCl solution. The resulting mixture is extracted with ethyl acetate. The organic phase is dried over Na$_2$SO$_4$, filtered and evaporated under vacuum. 1.6 g of the title product are isolated in the form of a white solid.

Preparation 17

2-(1,2,3,6-tetrahydropyridin-4-yl)quinoline hydrochloride

By performing the process as described in Preparation 10, but using quinolin-2-yl trifluoromethanesulfonate instead of methyl 5-bromobenzo[b]thiophene-2-carboxylate, the title compound is obtained in the form of a white solid.

Preparation 18

(3S,5R)-3,5-dimethyl-1-(5-thiazol-2-ylpyridin-2-yl)piperazine

Step a) (3S,5R)-3,5-dimethyl-1-(5-iodopyridin-2-yl)piperazine

By performing the process as described in Preparation 1, but using 2-fluoro-5-iodopyridine instead of 2-chloro-5(trifluoromethyl)pyridine, the title compound is obtained in the form of an oil.

Step b) tert-Butyl (2S,6R)-2,6-dimethyl-4-(5-iodopyridin-2-yl)piperazine-1-carboxylate 0.35 g of the compound from step a), 0.26 g of (Boc)$_2$O and 0.46 ml of triethylamine are placed in 5 ml of DMF under a stream of nitrogen at 0° C. The mixture is heated at a temperature of 140° C. for 4 hours. The solvent is evaporated off. 0.49 g of crude product is isolated. The residue is purified by flash chromatography on a Biotage® column, using ethyl acetate as eluent. 0.43 g of the title compound is isolated having the form of a pale yellow oil.

Step c) tert-Butyl (2S,6R)-2,6-dimethyl-4-[5-(4,4,5,5-tetramethyl-[1,3,2]dioxaborolan-2-yl)pyridin-2-yl]piperazine-1-carboxylate 0.43 g of the compound from step b), 0.29 g of bis(pinacol) diboron, 0.026 g of palladium Cl$_2$ (dppf)$_2$.CH$_2$Cl$_2$ and 0.31 g of potassium acetate are placed in 10 ml of DMSO in a round-bottomed flask under a stream of nitrogen. The mixture is heated at 85° C. for 2 hours. The resulting mixture is poured into saturated aqueous NaCl solution and extracted with ethyl acetate. The organic phase is dried over Na$_2$SO$_4$, filtered and evaporated under vacuum. 0.32 g of an oily material is isolated, and this material is purified by flash chromatography on a Biotage® column, using 9/1 cyclohexane/ethyl acetate as eluent. 0.28 g of a yellowish solid is isolated.

Step d) tert-Butyl 2S,6R-2,6-dimethyl-4-(5-thiazol-2-ylpyridin-2-yl)piperazine-1-carboxylate 0.28 g of the compound from step c), 0.092 g of 2-bromothiazole, 0.032 g of palladiumTetrakis (PdP(Ph3)$_4$) and 0.094 g of sodium bicarbonate are placed in 20 ml of DME and 3 ml of water in a round-bottomed flask under a stream of nitrogen. The mixture is heated at the reflux temperature for 7 hours. The resulting mixture is poured into saturated aqueous NaCl solution and extracted with ethyl acetate. The organic phase is dried over Na$_2$SO$_4$, filtered and evaporated under vacuum. 0.36 g of an oily material is isolated, and this material is purified by flash chromatography on a Biotage® column, using 9/1 cyclohexane/ethyl acetate as eluent. 0.2 g of a yellowish oil is isolated.

Step e) (3S,5R)-3,5-dimethyl-1-(5-thiazol-2-ylpyridin-2-yl)piperazine trifluoroacetate The compound from step d) (0.2 g) is dissolved slowly in 5 ml of trifluoroacetic acid at 0° C. The mixture is then stirred for 2 hours at room temperature. The trifluoroacetic acid is evaporated off under vacuum to give 0.15 g of the title compound in the form of a beige-colored solid.

Preparation 19

[3-oxo-4-(5-trifluoromethylpyridine-2-yl)piperazin-1-yl]acetic acid

Step a) Benzyl [3-oxo-4-(5-trifluoromethylpyridine-2-yl)piperazin-1-yl]acetate 1.12 g of 1-(5-trifluoromethylpyridin-2-yl)piperazin-2-one, 40 ml of THF and 0.87 ml of benzyl bromoacetate are placed in 1.5 ml of triethylamine in a round-bottomed flask equipped with a magnetic stirrer. The mixture is reacted under a stream of nitrogen overnight at room temperature. The solvent is evaporated off and the residue is purified by flash chromatography on a Biotage® column, using 1/1 hexane/ethyl acetate as eluent. 2.9 g of title product are isolated in the form of a white solid.

Step b) [3-oxo-4-(5-trifluoromethylpyridine-2-yl)piperazin-1-yl]acetic acid 1 g of the product from the preceding step is dissolved in 150 ml of ethanol, followed by addition of 0.15 g of 10% Pd/C. The mixture is reacted under a stream of hydrogen for 4 hours at a temperature of 40° C. The resulting mixture is filtered and evaporated under vacuum to give 0.74 g of the title compound in the form of a white solid.

EXAMPLE 1

Compound 34

1-(4-Benzofuran-7-yl-3,6-dihydro-2H-pyridin-1-yl)-2-[(2S,6R)-2,6-dimethyl-4-(5-trifluoromethylpyridin-2-yl)piperazin-1-yl]ethanone 0.18 g of the compound obtained in Preparation 8 (compound of formula (II)), 0.17 g of the compound obtained in Preparation 1 (compound of formula (III)), 0.1 g of potassium carbonate and 0.04 g of NaI are reacted together in 3 ml of DMF. The reaction is performed using a CEMdiscover microwave initiator for 30 minutes at 160° C. The mixture is poured into water and extracted with ethyl acetate. The organic phase is dried over Na$_2$SO$_4$, filtered and evaporated under vacuum. 0.36 g of an oily material is isolated. It is purified on a column by flash chromatography using a Biotage® column eluted with a 6/4 cyclohexane/ethyl acetate mixture. 0.180 g of a pale yellow solid is isolated, and is crystallized from ethyl ether. The product is filtered off to give 0.08 g of title product in the form of a white solid.

M.p.: 138-139° C.

NMR Machine b). δ (ppm, DMSO-d6): 1.06 (m, 6H); 2.56-2.79 (m, 4H); 3.19 (m, *), 3.73 (m, 4H); 4.18 (m, 3H); 4.31 (m, 1H); 6.57 (m, 1H); 6.95 (d, J=9.2 Hz, 1H); 6.99 (d, J=1.8 Hz, 1H); 7.27 (m, 2H); 7.58 (d, J=7.2 Hz, 1H); 7.76 (dd, J=9.2 and 2.2 Hz, 1H); 8.01 (d, J=1.7 Hz, 1H); 8.39 (bs, 1H).

EXAMPLE 2

Compound 4

1-(4-Benzo[b]thiophen-7-yl-3,6-dihydro-2H-pyridin-1-yl)-2-[(2S,6R)-2,6-dimethyl-4-(5-trifluoromethylpyridin-2-yl)piperazin-1-yl]ethanone and the oxalate thereof By performing the process as described in Example 1, but using the compound of Preparation 7 instead of the compound of Preparation 8, the title compound is obtained.

It is dissolved in acetone and a solution of oxalic acid in acetone is added, and the oxalate is obtained in the form of a white solid.

M.p.: 60-61° C.

NMR: (Machine b). δ (ppm, DMSO-d6): 1.17 (m, 6H), 2.60+2.68 (2×m, 2H); 2.97 (m, *); 3.36 (m, *); 3.76 (m, *); 4.00 (m, *); 4.14-4.43 (m, *); 6.30 (bs, 1H); 7.03 (d, J=9.0 Hz, 1H); 7.32 (d, J=7.1 Hz, 1H); 7.42 (t, J=7.6 Hz, 1H); 7.51 (d, J=5.3 Hz, 1H); 7.77 (d, J=5.5 Hz, 1H); 7.83 (m, 2H); 8.43 (bs, 1H).

EXAMPLE 3

Compound 14

1-(4-Benzofuran-7-yl-3,6-dihydro-2H-pyridin-1-yl)-2-[(2R,5S)-2,5-dimethyl-4-(5-trifluoromethylpyridin-2-yl)piperazin-1-yl]ethanone and the oxalate thereof By performing the process as described in Example 1, but using the compound of Preparation 2 instead of the compound of Preparation 1, the title compound is obtained.

It is dissolved in acetone, a solution of oxalic acid in acetone is added and the oxalate is obtained in the form of a white solid.

M.p.: 130-131° C.

NMR (Machine b). δ (ppm, DMSO-d6): 1.02 (m, 3H); 1.15-1.32 (m, 3H); 2.64 (m, 2H); 2.78 (m, 1H); 2.92 (m, 1H); 2.90 (m, 1H); 3.26 (m, *); 3.34-3.67 (m, *); 3.66-3.99 (m, *); 4.07-4.54 (m, *); 4.64 (m, *); 6.58 (m, 1H); 6.90 (m, 1H); 6.98 (d, J=1.9 Hz, 1H); 7.20-7.33 (m, 2H); 7.58 (d, J=7.2 Hz, 1H); 7.76 (m, 1H); 8.00 (d, J=1.8 Hz, 1H); 8.39 (m, 1H).

EXAMPLE 4

Compound 69

Methyl 6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinate 0.47 g of the compound obtained in Preparation 7 (compound of formula (II)), 0.45 g of the compound obtained in Preparation 5 (compound of formula (III)), 0.57 ml of diisopropylethylamine and 18 ml of DMF are reacted together. The mixture is heated at 100° C. for 3 hours. It is poured into water and extracted with ethyl acetate. The organic phase is dried over $Na_2SO_4$, filtered and evaporated under vacuum. 0.58 g of a solid material is isolated. It is purified on a column by flash chromatography, eluting with a 1/1 hexane/ethyl acetate mixture. 0.24 g of the title product is isolated. It is treated with diethyl ether and filtered to give 0.21 g of a white solid.

M.p.: 153-154° C.

NMR (Machine a). δ (ppm, DMSO-d6): 1.87 (m, 2H), 1.98 (m, 2H); 2.40 (m, 2H); 2.56 (m, 1H); 2.71 (m, 3H); 3.17+3.20 (2×s, 2H); 3.69-3.88 (m, 5H); 4.16 (s, 1H); 4.42 (s, 1H); 4.67 (bs, 2H); 6.29+6.32 (2×m, 1H); 6.78 (m, 1H); 7.31 (d, J=7.2 Hz, 1H); 7.42 (t, J=7.6 Hz, 1H); 7.50 (d, J=54 Hz, 1H); 7.77 (d, J=5.3 Hz, 1H); 7.82 (d, J=7.5 Hz, 1H); 7.93 (d, J=8.7 Hz, 1H); 8.64 (bs, 1H).

EXAMPLE 5

Compound 23

1-(4-Benzofuran-7-yl-3,6-dihydro-2H-pyridin-1-yl)-2-[8-(5-fluoropyrimidin-2-yl)-3,8-diazabicyclo[3.2.1]oct-3-yl]ethanone By performing the process as described in Example 4, but using the compound of Preparation 8 instead of the compound of Preparation 7, and the compound of Preparation 3 instead of the compound of Preparation 5, the title compound is obtained in the form of a white solid.

M.p.: 174-175° C.

NMR (Machine a). δ (ppm, DMSO-d6): 1.71-2.03 (m, 4H); 2.39 (m, 2H); 2.57-2.80 (m, 4H); 3.16+3.19 (2×s, 2H); 3.73+3.82 (2×m, 2H); 4.17 (bs, 1H); 4.42 (bs, 1H); 4.60 (m, 2H); 6.56+6.59 (2×m, 1H); 6.98 (d, J=2.3 Hz, 1H); 7.27 (m, 2H); 7.58 (dd, J=7.35 and 1.8 Hz, 1H); 8.01 (d, J=2.1 Hz, 1H); 8.44 (m, 2H).

EXAMPLE 6

Compound 71

6-{3-[2-(4-Benzo[b]thiophen-7-yl-3,6-dihydro-2H-pyridin-1-yl)-2-oxoethyl]-3,8-diazabicyclo[3.2.1]oct-8-yl}nicotinic acid 0.147 g of the compound of Example 4 is dissolved in 2 ml of aqueous 3N HCl solution. The mixture is heated at the reflux temperature for 2 hours. 2 ml of aqueous 3N HCl are added. The mixture is heated at the reflux temperature for 1 hour. The resulting mixture is washed with ethyl ether. The pH is adjusted to 6 with $NaHCO_3$ solution and the resulting mixture is extracted with ethyl acetate. The organic phase is dried and evaporated to give 200 mg of an oily material. This material is treated with diethyl ether and filtered to give 0.015 g of a pale yellow solid corresponding to the title product.

M.p.: 121-122° C.

NMR (Machine b). δ (ppm, DMSO-d6): 1.75-2.06 (m, 4H); 2.41 (m, 2H); 2.56 (m, **); 2.70 (m, 3H); 3.12-3.33 (m, *); 3.68-3.90 (m, 2H); 4.16 (bs, 1H); 4.42 (bs, 1H); 4.66 (bs, 2H); 6.29 (m, 1H); 6.78 (m, 1H); 7.31 (d, J=7 Hz, 1H); 7.42 (dd→t, J=~8 Hz, 1H); 7.50 (d, J=5.6 Hz, 1H); 7.77 (d, J=5.4 Hz, 1H); 7.82 (d, J=8 Hz, 1H); 7.91 (m, 1H); 8.63 (bs, 1H); 11.72-12.49 (bs, 1H).

EXAMPLE 7

Compound 32

4-[2-(4-Benzofuran-7-yl-3,6-dihydro-2H-pyridin-1-yl)-2-oxoethyl]-1-(5-trifluoromethylpyridin-2-yl)piperazin-2-one By performing the process as described in Example 4, but using the compound of Preparation 8 instead of the compound of Preparation 7, and the compound of Preparation 6 instead of the compound of Preparation 5, the title compound is obtained in the form of a white solid.

M.p.: 151-152° C.

NMR (Machine a). δ (ppm, DMSO-d6): 2.64 (m, 0.9H); 2.73 (m, 1.1H); 2.99 (m, 2H); 3.51 (s, 3H); 3.77 (m, 2H); 3.98 (m, 2H); 4.22 (s, 1.1H); 4.33 (s, 0.9H); 6.57 (bs, 1H); 6.98 (d, J=2.2 Hz, 1H); 7.22-7.34 (m, 2H); 7.58 (bd, J=7.5 Hz, 1H); 7.99 (bs, 1H); 8.22 (m, 2H); 8.84 (m, 1H).

EXAMPLE 8

Compound 20

1-(4-Quinolin-8-yl-3,6-dihydro-2H-pyridin-1-yl)-2-[4-(5-trifluoromethyl-pyridin-2-yl)piperazin-1-yl]ethanone and the oxalate thereof By performing the process as described in Example 4, but using the compound of Preparation 11 instead of the compound of Preparation 7, and 1-(5-trifluoromethylpyridin-2-yl)piperazine instead of the compound of Preparation 5, the title compound is obtained.

It is dissolved in acetone and a solution of oxalic acid in acetone is added, to give the oxalate in the form of an amorphous beige-colored solid.

NMR (Machine b). δ (ppm, DMSO-d6): 2.77+2.87 (2×m, 2H); 3.02 (m, 4H); 3.53-3.98 (m, *); 4.22 (m, 2H); 5.96 (m, 1H); 7.03 (d, J=9.1 Hz, 1H); 7.50-7.65 (m, 3H); 7.86 (dd, J=9.0 and 2.1 Hz, 1H); 7.92 (m, 1H); 8.38 (dd, J=8.2 and 1.8 Hz, 1H); 8.46 (bs, 1H); 8.90 (m, 1H).

EXAMPLE 9

Compound 45

1-[4-(2,3-Dihydrobenzo[1,4]dioxin-6-yl)-3,6-dihydro-2H-pyridin-1-yl]-2-[(2S,6R)-2,6-dimethyl-4-(6-trifluoromethylpyridin-3-yl)piperazin-1-yl]ethanone By performing the process as described in Example 1, but using the compound of Preparation 12 instead of the compound of Preparation 8 and the compound of Preparation 4 instead of the compound of Preparation 1, the title compound is obtained in the form of a white solid.

M.p.: 200-201° C.

NMR (Machine a). δ (ppm, DMSO-d6): 1.05 (m, 6H); 2.39+2.50 (2×m, **); 2.60 (m, 2H); 3.21-3.32 (m, *); 3.56-3.73 (m, 4H); 3.77 (m, 2H); 4.05+4.18 (2×m, 2H); 4.24 (s, 4H); 6.05 (m, 1H); 6.82 (d, J=8.4 Hz, 1H); 6.89-6.96 (m, 2H); 7.39 (dd, J=8.8 and 2.6 Hz, 1H); 7.60 (d, J=8.8 Hz, 1H); 8.39 (d, J=2.7 Hz, 1H).

EXAMPLE 10

Compound 63

1-(5-Benzofuran-7-yl-3,6-dihydro-2H-pyridin-1-yl)-2-[(2S,6R)-2,6-dimethyl-4-(5-trifluoromethylpyridin-2-yl)piperazin-1-yl]ethanone By performing the process as described in Example 1, but using the compound of Preparation 9 instead of the compound of Preparation 8, the title compound is obtained in the form of a white solid.

M.p.: 129-130° C.

NMR (Machine a). δ (ppm, DMSO-d6): 1.06 (m, 6H); 2.33+2.44 (2×m, 2H); 2.71 (m, 2H); 3.19 (m, *); 3.68 (m, 2H); 3.73 (s, 2H); 4.17 (m, 2H); 4.47+4.58 (2×bs, 2H); 6.63 (bs, 1H); 6.94 (m, 1H); 6.70 (bs, 1H); 7.22-7.39 (m, 2H); 7.59 (d, J=7.4 Hz, 1H); 7.75 (bd, J=9.0 Hz, 1H); 8.02 (bs, 1H); 8.38 (bs, 1H).

EXAMPLE 11

Compound 67

Methyl 5-(1-{2-[(2S,6R)-2,6-dimethyl-4-(5-trifluoromethylpyridin-2-yl)piperazin-1-yl]acetyl}-1,2,3,6-tetrahydropyridin-4-yl)benzo[b]thiophene-2-carboxylate and the oxalate thereof By performing the process as described in Example 1, but using the compound of Preparation 10 instead of the compound of Preparation 8, the title compound is obtained.

It is dissolved in acetone and a solution of oxalic acid in acetone is added, to give the oxalate in the form of an amorphous beige-colored solid.

NMR (Machine b). δ (ppm, DMSO-d6): 1.15 (m, 6H); 2.58+2.68 (2×m, 2H); 2.95 (m, 2H); 3.35 (m, 2H); 3.74 (m, *); 3.82-4.08 (m, *); 4.12-4.40 (m, *); 6.31 (m, 1H); 7.03 (d, J=9.0 Hz, 1H); 7.70 (m, 1H); 7.83 (bd, J=9.1 Hz, 1H); 8.01-8.11 (m, 2H); 8.20 (bs, 1H); 8.43 (bs, 1H).

EXAMPLE 12

Compound 83

4-[2-(3-Benzofuran-7-yl-2,5-dihydropyrrol-1-yl)-2-oxoethyl]-1-(5-trifluoromethylpyridin-2-yl)piperazin-2-one By performing the process as described in Example 4, but using the compound of Preparation 13 instead of the compound of Preparation 7, and the compound of Preparation 6 instead of the compound of Preparation 5, the title compound is obtained in the form of a white solid.

M.p. 184-186° C.

NMR (Machine b). δ (ppm, DMSO-d6): 2.89-3.12 (m, 4H); 3.45-3.59 (m, 4H); 3.80-4.02 (m, 4H); 4.74+4.83 (2×s, 2H); 7.51 (m, 3H); 8.20 (m, 2H); 8.37 (m, 2H); 8.65-8.88 (m, 2H).

EXAMPLE 13

Compound 89

3-(6-{3-[2-(4-Benzofuran-7-yl-3,6-dihydro-2H-pyridin-1-yl)-2-oxoethyl]-3,8-diazabicyclo[3.2.1]oct-8-yl}pyridin-3-yl)-4H-[1,2,4]oxadiazol-5-one By performing the process as described in Example 4, but using the compound of Preparation 8 instead of the compound of Preparation 7, and the compound of Preparation 15 instead of the compound of Preparation 5, the title compound is obtained in the form of a white solid.

M.p.: 230-232° C.

NMR: (Temp. B). δ (ppm, DMSO-d6): 1.76-2.04 (m, 4H), 2.41 (m, 2H), 2.56-2.81 (m, 4H), 3.17+3.21 (2×s, 2H), 3.73 (m, 1H), 3.81 (m, 1H), 4.17 (m, 1H), 4.42 (m, 1H), 4.64 (m, 2H), 6.56 (m, 0.5H), 6.61 (m, 0.5H), 6.89 (m, 1H), 6.99 (d, J=2.2 Hz, 1H), 7.24-7.32 (m, 2H), 7.58 (dd, J=7.3 and 1.4 Hz, 1H), 7.82 (m, 1H), 8.02 (m, 1H), 8.48 (m, 1H), 12.69 (bs, 1H).

EXAMPLE 14

Compound 51

Methyl 6-{(3R,5S)-4-[2-(4-benzofuran-7-yl-3,6-dihydro-2H-pyridin-1-yl)-2-oxoethyl]-3,5-dimethylpiperazin-1-yl}nicotinate By performing the process as described in Example 1, but using the compound of Preparation 14 instead of the compound of Preparation 1, the title compound is obtained.

It is dissolved in acetone and a solution of oxalic acid in acetone is added, to give the oxalate in the form of an amorphous white solid.

NMR: (Machine b, Temp. A). δ (ppm, DMSO-d6): 1.19 (m, 6H), 2.67+2.76 (2×m, 2H), 3.04 (m, ), 3.43 (m, ), 3.58-4.58 (m, **), 6.58 (m, 1H), 6.88-7.12 (m, 2H), 7.28 (m, 2H), 7.59 (m, 1H), 7.90-8.12 (m, 2H), 8.68 (m, 1H).

EXAMPLE 15

Compound 57

6-{(3S,5R)-4-[2-(4-Benzofuran-7-yl-3,6-dihydro-2H-pyridin-1-yl)-2-oxoethyl]-3,5-dimethylpiperazin-1-yl}nicotinic acid By performing the process as described in Example 6, but using the compound of Example 14 instead of the compound of Example 4, the title compound is obtained in the form of an oily material. It is treated with diethyl ether and filtered, to give a pale yellow solid corresponding to the title product.

M.p.: 272-274° C.

NMR: (Temp. B). δ (ppm, DMSO-d6): 1.06 (m, 6H), 2.55-2.76 (m, 4H), 3.17 (m, 2H), 3.72 (m, 4H), 4.18 (m, 3H), 3.41 (s, 1H), 6.57 (m, 1H), 6.81 (d, J=9.0 Hz, 1H), 7.00 (d, J=2.1

Hz, 1H), 7.22-7.32 (m, 2H), 7.58 (d, J=7.4 Hz, 1H), 7.93 (d, J=9.0 Hz, 1H), 8.02 (s, 1H), 8.62 (m, 1H).

EXAMPLE 16

Compound 118

4-[2-Oxo-2-(4-thieno[3,2-c]pyridin-4-yl-3,6-dihydro-2H-pyridin-1-yl)ethyl]-1-(5-trifluoromethylpyridin-2-yl)piperazin-2-one 0.11 g of the compound of Preparation 19 is suspended in a round-bottomed flask equipped with a magnetic stirrer, in 13 ml of dichloromethane. 0.1 g of 4-(1,2,3,6-tetrahydropyridin-4-yl)thieno[3,2-c]pyridine, 0.19 ml of triethylamine and 0.15 g of BOP are added. The mixture is reacted for 1 hour at room temperature.

It is then poured into water and extracted with dichloromethane. The organic phase is dried over $Na_2SO_4$, filtered and evaporated under vacuum. 0.22 g of an oily material is isolated. It is purified on a column by flash chromatography using a Biotage® column eluted with ethyl acetate. 0.7 g of white solid is isolated.

M.p.: 145-148° C.

NMR: (Machine a, Temp. B). δ (ppm, DMSO-d6): 2.69 (m, 0.9H), 2.79 (m, 1.1H), 3.00 (m, 2H), 3.51 (m, 4H), 3.77 (m, 2H), 3.97 (m, 2H), 4.25 (m, 1.1H), 4.35 (m, 0.9H), 6.34+6.37 (2×m, 1H), 7.75 (m, 1H), 7.84+7.88 (2×m, 1H), 7.97 (m, 1H), 8.22 (m, 2H), 8.40 (m, 1H), 8.84 (m, 1H).

EXAMPLE 17

Compound 119

1-(4-Benzofuran-7-yl-3,6-dihydro-2H-pyridin-1-yl)-2-[(2S,6R)-2,6-dimethyl-4-(5-thiazol-2-ylpyridin-2-yl)piperazin-1-yl]ethanone oxalate By performing the process as described in Example 1, but using the compound of Preparation 18 instead of the compound of Preparation 1, the title compound is obtained in free base form. It is dissolved in acetone and a solution of oxalic acid in acetone is then added. The title product is obtained in the form of a white solid.

M.p.: 140-145° C.

NMR: (Machine a, Temp. B). δ (ppm, DMSO-d6): 1.21 (m, 6H), 2.67 (m, *), 2.77 (m, *), 2.91-3.95 (m, *), 4.04-4.47 (m, *), 6.59 (m, 1H), 7.00 (d, J=2.1 Hz, 1H), 7.05 (m, 1H), 7.27 (m, 1H), 7.32 (m, 1H), 7.59 (d, J=7.4 Hz, 1H), 7.68 (bd, J=3.2 Hz, 1H), 7.86 (bd, J=3.2 Hz, 1H), 8.03 (bd, 1H), 8.08 (m, 1H), 8.71 (bs, 1H)

EXAMPLE 18

Compound 121

2-[(2S,6R)-2,6-Dimethyl-4-(5-trifluoromethylpyridin-2-yl)piperazin-1-yl]-1-(4-quinolin-2-yl-3,6-dihydro-2H-pyridin-1-yl)ethanone By performing the process as described in Example 16, but using the compound of Preparation 16 instead of the compound of Preparation 19, and the compound of Preparation 17 instead of 4-(1,2,3,6-tetrahydropyridin-4-yl)thieno[3,2-c]pyridine, the title compound is obtained in the form of a white solid.

M.p.: 94-95° C.

NMR: (Machine a, Temp. B). δ (ppm, DMSO-d6): 1.06 (m, 6H), 2.66-2.78 (m, 3H), 2.85 (m, 1H), 3.20 (m, 2H), 3.66-3.79 (m, 4H), 4.20 (m, 3H), 4.35 (m, 1H), 6.89 (m, 1H), 6.95 (d, J=9.1 Hz, 1H), 7.56 (m, 1H), 7.72-7.79 (m, 2H), 7.87 (d, J=8.7 Hz, 1H), 7.92-7.99 (m, 2H), 8.33 (m, 1H), 8.39 (m, 1H).

The following table describes the examples obtained by application and/or adaptation of methods described using suitable reagents and starting materials:

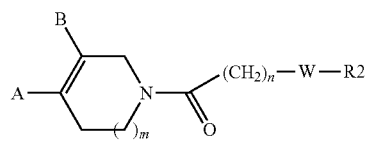

(I)

| No. | A | B | m | W | R2 | n | Salt | M.P. ° C. | LCMS |
|---|---|---|---|---|---|---|---|---|---|
| 1 | benzothiophen-7-yl | H | 1 | (2S,6R)-2,6-dimethylpiperazine | 2-methylpyrazine | 1 | oxalate | 60-61 | MH+ 448 r.t. 8.4' Method A |
| 2 | benzothiophen-7-yl | H | 1 | 2,5-diazabicyclo | 2-methylpyrimidine | 1 | HCl | 111-112 | MH+ 446 r.t. 8.4' Method A |
| 3 | benzothiophen-5-yl | H | 1 | 2,5-diazabicyclo | 2-methylpyrimidine | 1 | — | | MH+ 446 r.t. 9.5' Method A |

-continued (I)

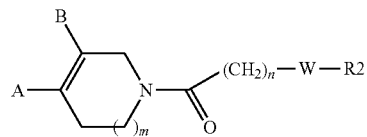

| No. | A | B | m | W | R2 | n | Salt | M.P. ° C. | LCMS |
|---|---|---|---|---|---|---|---|---|---|
| 4 | 7-methylbenzothiophene | H | 1 | (2S,5R)-dimethylpiperazine | 2-methyl-5-CF₃-pyridine | 1 | oxalate | — | MH+ 515 r.t. 19.1' Method A |
| 5 | 5-methylbenzothiophene | H | 1 | (2S,5R)-dimethylpiperazine | 2-methylpyrazine | 1 | oxalate | 101-102 | MH+ 448 r.t. 16.4' Method G |
| 6 | 7-methylbenzothiophene | H | 1 | (2S,5R)-dimethylpiperazine | 2-methylpyrazine | 1 | oxalate | 96-97 | MH+ 448 r.t. 8.6' Method A |
| 7 | 5-methylbenzothiophene | H | 1 | (2S,5R)-dimethylpiperazine | 2-methyl-5-CF₃-pyridine | 1 | — | — | MH+ 515 r.t. 22.7' Method C |
| 8 | 7-methylbenzothiophene | H | 1 | diazabicyclo | 2-methyl-5-CF₃-pyridine | 1 | — | 162-163 | MH+ 513 r.t. 14.6' Method B |
| 9 | 7-methylbenzothiophene | H | 1 | (2S,5R)-dimethylpiperazine | 2-methyl-5-CF₃-pyridine | 1 | oxalate | 107-108 | MH+ 515 r.t. 22.2' Method C |
| 10 | 2,7-dimethylbenzothiophene | H | 1 | (2S,5R)-dimethylpiperazine | 2-methyl-5-CF₃-pyridine | 1 | oxalate | 93-94 | MH+ 529 r.t. 12.7' Method B |

-continued

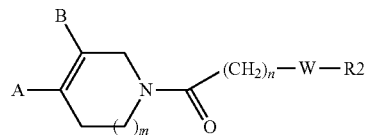

| No. | A | B | m | W | R2 | n | Salt | M.P. °C. | LCMS |
|---|---|---|---|---|---|---|---|---|---|
| 11 | 7-methyl-2-propyl-benzothiophene | H | 1 | (2S,5R)-2,5-dimethylpiperazine | 6-methyl-3-CF3-pyridine | 1 | oxalate | 90-91 | MH+ 557 r.t. 17.0' Method D |
| 12 | 7-methyl-benzothiophene | H | 1 | 2,5-diazabicyclo[2.2.1] | 6-methyl-3-CF3-pyridine | 1 | oxalate | 105-106 | MH+ 499 r.t. 12.7' Method D |
| 13 | 6-methyl-benzothiophene | H | 1 | (2R,5S)-2,5-dimethylpiperazine | 6-methyl-3-CF3-pyridine | 1 | oxalate | 141-143 | MH+ 515 r.t. 6.3' Method A |
| 14 | 7-methyl-benzofuran | H | 1 | (2R,5S)-2,5-dimethylpiperazine | 6-methyl-3-CF3-pyridine | 1 | oxalate | 130-131 | MH+ 499 r.t. 8.6' Method B |
| 15 | 2,5-dimethyl-benzothiophene | H | 1 | 2,5-diazabicyclo[2.2.1] | 2-methylpyrimidine | 1 | — | 171-173 | MH+ 460 r.t. 5.7' Method A |
| 16 | 2,5-dimethyl-benzothiophene | H | 1 | piperazine | 6-methyl-3-CF3-pyridine | 1 | — | 159 | MH+ 5.1 r.t. 7.6' Method A |
| 17 | 2,6-dimethyl-benzothiophene | H | 1 | 2-oxopiperazine | 6-methyl-3-CF3-pyridine | 1 | — | 141-143 | MH+ 515 r.t. 8.2' Method A |
| 18 | 2,5-dimethyl-benzothiophene | H | 1 | (2S,5R)-2,5-dimethylpiperazine | 6-methyl-3-CF3-pyridine | 1 | — | 162-163 | MH+ 529 r.t. 6.3' Method A |

-continued

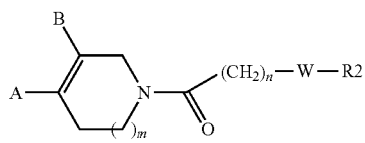
(I)

| No. | A | B | m | W | R2 | n | Salt | M.P. °C. | LCMS |
|---|---|---|---|---|---|---|---|---|---|
| 19 | 7-methylbenzothiophene | H | 1 | (2S,5R)-2,5-dimethylpiperazine | 2-methylquinoline | 1 | HCl | 192-193 | MH+ 497 r.t. 5.5' Method A |
| 20 | 8-methylquinoline | H | 1 | piperazine | 2-methyl-5-trifluoromethylpyridine | 1 | oxalate | — | MH+ 482 r.t. 4.7' Method A |
| 21 | 6-methyl-2,3-dihydro-1,4-benzodioxine | H | 1 | piperazine | 2-methyl-5-trifluoromethylpyridine | 1 | — | 142-143 | MH+ 489 r.t. 5.3' Method A |
| 22 | 2,5-dimethylbenzothiophene | H | 1 | 2,5-diazabicyclo[2.2.1]heptane | 5-fluoro-2-methylpyrimidine | 1 | — | 177-179 | MH+ 478 r.t. 6.7' Method A |
| 23 | 7-methylbenzofuran | H | 1 | 2,5-diazabicyclo[2.2.1]heptane | 5-fluoro-2-methylpyrimidine | 1 | — | 157-158 | MH+ 448 r.t. 5.6' Method C |
| 24 | 6-methyl-2,3-dihydro-1,4-benzodioxine | H | 1 | 2,5-diazabicyclo[2.2.1]heptane | 5-fluoro-2-methylpyrimidine | 1 | — | 163-165 | MH+ 466 r.t. 5.0' Method A |
| 25 | 4-methylthieno[3,2-c]pyridine | H | 1 | 2,5-diazabicyclo[2.2.1]heptane | 5-fluoro-2-methylpyrimidine | 1 | — | 167-168 | MH+ 465 r.t. 3.8' Method A |
| 26 | 3-methylbenzofuran | H | 1 | 2,5-diazabicyclo[2.2.1]heptane | 5-fluoro-2-methylpyrimidine | 1 | — | 207-210 | MH+ 448 r.t. 5.6' Method A |
| 27 | 3-methylindole | H | 1 | 2,5-diazabicyclo[2.2.1]heptane | 5-fluoro-2-methylpyrimidine | 1 | oxalate | 128-130 | MH+ 447 r.t. 4.8' Method A |

-continued

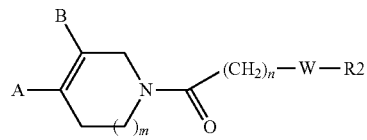
(I)

| No. | A | B | m | W | R2 | n | Salt | M.P. ° C. | LCMS |
|---|---|---|---|---|---|---|---|---|---|
| 28 | 6-fluoro-3-methylindole | H | 1 | diazabicyclic N-N | 5-fluoro-2-methylpyrimidine | 1 | oxalate | 95-96 | MH+ 465 r.t. 5.3' Method A |
| 29 | 3-methylbenzothiophene | H | 1 | diazabicyclic N-N | 5-fluoro-2-methylpyrimidine | 1 | — | 172-174 | MH+ 464 r.t. 5.5' Method A |
| 30 | 3-methylindole | H | 1 | piperazinone | 5-CF3-2-methylpyridine | 1 | — | 230-233 | MH+ 484 r.t. 6.8' Method A |
| 31 | 7-methylbenzothiophene | H | 1 | piperazinone | 5-CF3-2-methylpyridine | 1 | — | 143-146 | MH+ 501 r.t. 7.7' Method A |
| 32 | 7-methylbenzofuran | H | 1 | piperazinone | 5-CF3-2-methylpyridine | 1 | — | 151-152 | MH+ 485 r.t. 7.5' Method A |
| 33 | 7-methylbenzofuran | H | 1 | piperazine | 5-CF3-2-methylpyridine | 1 | — | 155-156 | MH+ 471 r.t. 5.7' Method A |
| 34 | 7-methylbenzofuran | H | 1 | (2R,5S)-dimethylpiperazine | 5-CF3-2-methylpyridine | 1 | — | 138-139 | MH+ 499 r.t. 5.8' Method A |
| 35 | 7-methylbenzofuran | H | 1 | (2R,5S)-dimethylpiperazine | 5-methylpyrimidine | 1 | — | 142-143 | MH+ 432 r.t. 4.6' Method A |

-continued

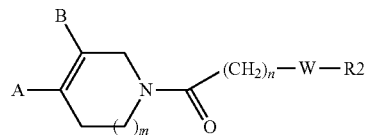
(I)

| No. | A | B | m | W | R2 | n | Salt | M.P. °C. | LCMS |
|---|---|---|---|---|---|---|---|---|---|
| 36 | 7-methyl benzofuran | H | 1 | (2S,5R)-dimethylpiperazine | 5-F, 2-methyl pyrimidine | 1 | HCl | 174-175 | MH+ 450 r.t. 5.4' Method A |
| 37 | 7-methyl benzofuran | H | 1 | (2S,5R)-dimethylpiperazine | 6-CF3, 3-methyl pyridine | 1 | — | 119-120 | MH+ 499 r.t. 5.7' Method A |
| 38 | 2,5-dimethyl benzothiophene | H | 1 | (2S,5R)-dimethylpiperazine | 5-F, 2-methyl pyrimidine | 1 | — | 205-206 | MH+ 480 r.t. 5.1' Method A |
| 39 | 2,5-dimethyl benzothiophene | H | 1 | (2S,5R)-dimethylpiperazine | 6-CF3, 3-methyl pyridine | 1 | — | 217-218 | MH+ 529 r.t. 5.4' Method A |
| 40 | 2,5-dimethyl benzothiophene | H | 1 | (2S,5R)-dimethylpiperazine | 5-methyl pyrimidine | 1 | — | 191-192 | MH+ 462 r.t. 4.5' Method A |
| 41 | 5-methyl benzothiophene | H | 1 | (2S,5R)-dimethylpiperazine | 5-methyl pyrimidine | 1 | — | 218-220 | MH+ 448 r.t. 4.5' Method A |
| 42 | 6-methyl benzothiophene | H | 1 | (2S,5R)-dimethylpiperazine | 5-F, 2-methyl pyrimidine | 1 | oxalate | — | MH+ 466 r.t. 5.6' Method E |
| 43 | 6-methyl benzothiophene | H | 1 | 3-oxopiperazine | 5-CF3, 2-methyl pyridine | 1 | — | 169-170 | MH+ 501 r.t. 7.0' Method A |

-continued

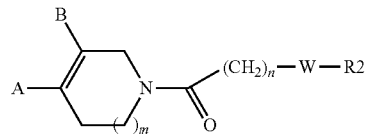

(I)

| No. | A | B | m | W | R2 | n | Salt | M.P. ° C. | LCMS |
|---|---|---|---|---|---|---|---|---|---|
| 44 | 6-methyl-2,3-dihydro-1,4-benzodioxine | H | 1 | (2S,5R)-2,5-dimethylpiperazine | 5-fluoro-2-methylpyrimidine | 1 | oxalate | 90-91 | MH+ 468 r.t. 4.3' Method A |
| 45 | 6-methyl-2,3-dihydro-1,4-benzodioxine | H | 1 | (2S,5R)-2,5-dimethylpiperazine | 2-CF3-5-methylpyridine | 1 | — | 200-201 | MH+ 517 r.t. 4.5' Method A |
| 46 | 5-methylbenzothiophene | H | 1 | piperazine | 5-CF3-2-methylpyridine | 1 | — | 170-171 | MH+ 487 r.t. 5.3' Method A |
| 47 | 5-methylbenzothiophene | H | 1 | (2S,5R)-2,5-dimethylpiperazine | 2-CF3-5-methylpyridine | 1 | — | 136-137 | MH+ 515 r.t. 6.3' Method E |
| 48 | 4-methylbenzothiophene | H | 1 | (2S,5R)-2,5-dimethylpiperazine | 5-COOH-2-methylpyridine | 1 | — | — | MH+ 491 r.t. 4.4' Method A |
| 49 | 6-methyl-2,3-dihydro-1,4-benzodioxine | H | 1 | 3-oxopiperazine | 5-CF3-2-methylpyridine | 1 | — | 161-162 | MH+ 503 r.t. 6.2' Method A |
| 50 | 7-methylbenzothiophene | H | 1 | piperazine | 5-CF3-2-methylpyridine | 1 | — | 120-121 | MH+ 487 r.t. 5.7' Method A |
| 51 | 7-methylbenzofuran | H | 1 | (2S,5R)-2,5-dimethylpiperazine | 5-COOMe-2-methylpyridine | 1 | oxalate | — | MH+ 489 r.t. 5.1' Method A |

-continued

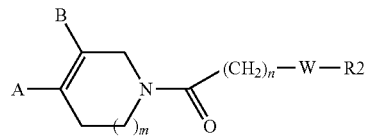
(I)

| No. | A | B | m | W | R2 | n | Salt | M.P. ° C. | LCMS |
|---|---|---|---|---|---|---|---|---|---|
| 52 | 5-methylbenzothiophene | H | 1 | (2S,5R)-2,5-dimethylpiperazine | 6-methyl-pyridine-3-COOMe | 1 | — | 130-132 | MH+ 505 r.t. 6.7' Method E |
| 53 | 7-methylbenzothiophene | H | 1 | (2S,5R)-2,5-dimethylpiperazine | 2-methyl-5-fluoro-pyrimidine | 1 | — | — | MH+ 466 r.t. 5.2' Method A |
| 54 | 7-methylbenzothiophene | H | 1 | (2S,5R)-2,5-dimethylpiperazine | 5-methyl-2-CF3-pyridine | 1 | HCl | 225-226 | MH+ 515 r.t. 5.6' Method A |
| 55 | 7-methylbenzothiophene | H | 1 | (2S,5R)-2,5-dimethylpiperazine | 5-methyl-pyrimidine | 1 | — | 195-196 | MH+ 448 r.t. 4.6' Method A |
| 56 | 5-methylbenzothiophene | H | 1 | (2S,5R)-2,5-dimethylpiperazine | 6-methyl-pyridine-3-COOH | 1 | — | — | MH+ 491 r.t. 6.1' Method A |
| 57 | 7-methylbenzofuran | H | 1 | (2S,5R)-2,5-dimethylpiperazine | 6-methyl-pyridine-3-COOH | 1 | — | 272-274 | MH+ 475 r.t. 4.7' Method A |
| 58 | 7-methylbenzothiophene | H | 1 | (2S,5R)-2,5-dimethylpiperazine | 6-methyl-pyridine-3-COOMe | 1 | HCl | 208-210 | MH+ 505 r.t. 6.6' Method E |
| 59 | 7-methylbenzothiophene | H | 1 | (2S,5R)-2,5-dimethylpiperazine | 6-methyl-pyridine-3-COOH | 1 | — | — | MH+ 491 r.t. 6.2' Method F |

-continued

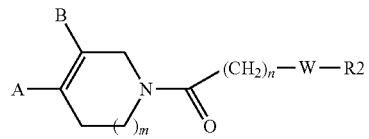
(I)

| No. | A | B | m | W | R2 | n | Salt | M.P. ° C. | LCMS |
|---|---|---|---|---|---|---|---|---|---|
| 60 | 5-methylbenzofuran | H | 1 | 3-oxopiperazine | 6-methyl-3-(trifluoromethyl)pyridine | 1 | — | 154-155 | MH+ 485 r.t. 7.3' Method A |
| 61 | 2,5-dimethylbenzothiophene | H | 1 | (2R,5S)-2,5-dimethylpiperazine | methyl 6-methylnicotinate | 1 | — | 148-150 | MH+ 519 r.t. 8.2' Method A |
| 62 | 2,5-dimethylbenzothiophene | H | 1 | (2R,5S)-2,5-dimethylpiperazine | 6-methylnicotinic acid | 1 | — | — | MH+ 505 r.t. 5.4' Method A |
| 63 | H | 7-methylbenzofuran | 1 | (2R,5S)-2,5-dimethylpiperazine | 6-methyl-3-(trifluoromethyl)pyridine | 1 | — | 129-130 | MH+ 499 r.t. 5.8' Method A |
| 64 | 7-methylbenzofuran | H | 1 | (2R,5S)-2,5-dimethylpiperazine | ethyl 6-methylnicotinate | 1 | HCl | — | MH+ 503 r.t. 5.5' Method A |
| 65 | 7-methylbenzofuran | H | 1 | 2,5-diazabicyclo[2.2.1]heptane | methyl 6-methylnicotinate | 1 | — | 158-159 | MH+ 487 r.t. 5.1' Method A |
| 66 | 7-methyl-2-(methoxycarbonyl)benzothiophene | H | 1 | (2R,5S)-2,5-dimethylpiperazine | 6-methyl-3-(trifluoromethyl)pyridine | 1 | HCl | 138-141 | MH+ 573 r.t. 6.0' Method A |
| 67 | 5-methyl-2-(methoxycarbonyl)benzothiophene | H | 1 | (2R,5S)-2,5-dimethylpiperazine | 6-methyl-3-(trifluoromethyl)pyridine | 1 | oxalate | — | MH+ 573 r.t. 6.0' Method A |

-continued

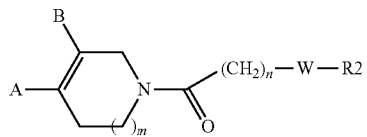

(I)

| No. | A | B | m | W | R2 | n | Salt | M.P. ° C. | LCMS |
|---|---|---|---|---|---|---|---|---|---|
| 68 | 5-methyl-2-propyl-benzothiophene | H | 1 | trans-2,5-dimethylpiperazine | 6-methyl-3-CF3-pyridine | 1 | — | 157-159 | MH+ 557 r.t. 6.8' Method A |
| 69 | 7-methyl-benzothiophene | H | 1 | 2,5-diazabicyclo[2.2.1]heptane | 6-methyl-3-COOMe-pyridine | 1 | — | 153-154 | MH+ 503 r.t. 5.5' Method A |
| 70 | 5-methyl-benzothiophene | H | 1 | 2,5-diazabicyclo[2.2.1]heptane | 6-methyl-3-COOMe-pyridine | 1 | — | 150-151 | MH+ 503 r.t. 5.5' Method A |
| 71 | 7-methyl-benzothiophene | H | 1 | 2,5-diazabicyclo[2.2.1]heptane | 6-methyl-3-COOH-pyridine | 1 | — | 121-122 | MH+ 489 r.t. 5.0' Method A |
| 72 | 7-fluoro-5-methyl-benzofuran | H | 1 | trans-2,5-dimethylpiperazine | 6-methyl-3-CF3-pyridine | 1 | oxalate | — | MH+ 517 r.t. 5.6' Method A |
| 73 | 2,3,6-trimethyl-benzofuran | H | 1 | trans-2,5-dimethylpiperazine | 6-methyl-3-CF3-pyridine | 1 | oxalate | — | MH+ 527 r.t. 6.1' Method A |
| 74 | 2-methyl-quinoline | H | 1 | trans-2,5-dimethylpiperazine | 6-methyl-3-CF3-pyridine | 1 | — | — | MH+ 510 r.t. 4.5' Method A |
| 75 | 6-methyl-benzofuran | H | 1 | piperazine | 5-methyl-pyrazine | 1 | — | — | MH+ 404 r.t. 11.5' Method H |

-continued

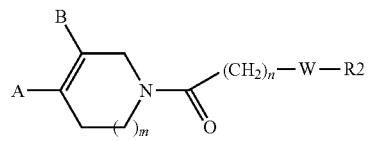

(I)

| No. | A | B | m | W | R2 | n | Salt | M.P. °C. | LCMS |
|---|---|---|---|---|---|---|---|---|---|
| 76 | thieno[3,2-c]pyridine-4-methyl | H | 1 | diazabicyclo piperazine | 6-methyl-pyridine-3-COOMe | 1 | — | 170-171 | MH+ 504 r.t. 3.7' Method A |
| 77 | 2,6-dimethyl-benzothiophene | H | 1 | diazabicyclo piperazine | 6-methyl-pyridine-3-COOMe | 1 | — | 179-180 | MH+ 517 r.t. 5.8' Method A |
| 78 | 7-methyl-benzofuran | H | 1 | N,N'-dimethyl-homopiperazine | 3-methyl-pyridine | 1 | oxalate | 100-101 | MH+ 417 r.t. 3.4' Method A |
| 79 | thieno[3,2-c]pyridine-4-methyl | H | 1 | diazabicyclo piperazine | 6-methyl-pyridine-3-COOH | 1 | — | 159-160 | MH+ 490 r.t. 3.8' Method A |
| 80 | 2,6-dimethyl-benzothiophene | H | 1 | diazabicyclo piperazine | 6-methyl-pyridine-3-COOH | 1 | — | 160-161 | MH+ 503 r.t. 8.5' Method A |
| 81 | 7-methyl-benzofuran | H | 0 | diazabicyclo piperazine | 6-methyl-pyridine-3-COOMe | 1 | — | 169-170 | MH+ 473 r.t. 5.0' Method A |
| 82 | 7-methyl-benzothiophene | H | 0 | diazabicyclo piperazine | 6-methyl-pyridine-3-COOMe | 1 | — | 172-173 | MH+ 489 r.t. 5.17' Method A |
| 83 | 7-methyl-benzofuran | H | 0 | 3-oxo-piperazine | 6-methyl-5-CF$_3$-pyridine | 1 | — | 184-186 | MH+ 471 r.t. 10.9' Method A |
| 84 | 7-methyl-benzofuran | H | 0 | diazabicyclo piperazine | 6-methyl-pyridine-3-COOH | 1 | — | 188-189 | MH+ 459 r.t. 4.81' Method A |

-continued

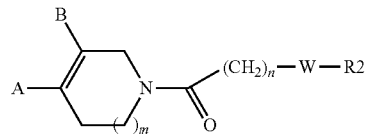
(I)

| No. | A | B | m | W | R2 | n | Salt | M.P. °C. | LCMS |
|---|---|---|---|---|---|---|---|---|---|
| 85 | 7-methylbenzothiophene | H | 1 | diazabicyclic piperazine | 6-methylpyridine-3-COOH | 1 | — | 191-192 | MH+ 489 r.t. 5.22' Method A |
| 86 | 7-methylbenzothiophene | H | 0 | diazabicyclic piperazine | 6-methylpyridine-3-COOH | 1 | — | 189-190 | MH+ 475 r.t. 4.97' Method A |
| 87 | 6-methyl-2,3-dihydrobenzodioxine | H | 1 | diazabicyclic piperazine | 6-methylpyridine-3-COOMe | 1 | — | 172-174 | MH+ 505 r.t. 4.77' Method A |
| 88 | 7-methylbenzothiophene | H | 1 | (2S,5S)-2,5-dimethylpiperazine | 2-methylpyrimidine-5-COOH | 1 | HCl | 275-278 | MH+ 492 r.t. 4.65' Method A |
| 89 | 7-methylbenzofuran | H | 1 | diazabicyclic piperazine | 3-(6-methylpyridin-3-yl)-1,2,4-oxadiazol-5(4H)-one | 1 | — | 230-232 | MH+ 513 r.t. 4.86' Method A |
| 90 | 7-methylbenzothiophene | H | 1 | diazabicyclic piperazine | 3-(6-methylpyridin-3-yl)-1,2,4-oxadiazol-5(4H)-one | 1 | — | 215-217 | MH+ 529 r.t. 5.07' Method A |
| 91 | 2,6-dimethylbenzothiophene | H | 1 | diazabicyclic piperazine | 6-methylpyridine-3-CN | 1 | — | 171-172 | MH+ 484 r.t. 5.87' Method A |
| 92 | 7-methylbenzofuran | H | 1 | (2S,5S)-2,5-dimethylpiperazine | 3-chloro-2-methyl-5-(trifluoromethyl)pyridine | 1 | — | 130-131 | MH+ 533 r.t. 5.75' Method A |

-continued

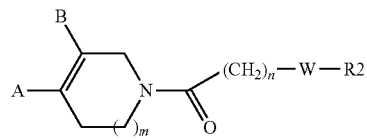
(I)

| No. | A | B | m | W | R2 | n | Salt | M.P. ° C. | LCMS |
|---|---|---|---|---|---|---|---|---|---|
| 93 | 7-methylbenzofuran | H | 1 | 2,5-diazabicyclo | 3-methylpyridine | 1 | — | 121-123 | MH+ 429 r.t. 4.06' Method A |
| 94 | 7-methylbenzofuran | H | 1 | 2,5-diazabicyclo | 6-methyl-3-cyanopyridine | 1 | — | 184-185 | MH+ 454 r.t. 5.35' Method A |
| 95 | 7-methylbenzofuran | H | 1 | 2,5-diazabicyclo | 2-methyl-5-CF3-pyridine | 1 | HCl | — | MH+ 483 r.t. 5.05' Method A |
| 96 | 2,5-dimethylbenzothiophene | H | 1 | 2,5-diazabicyclo | cyclobutyl 6-methylnicotinate | 1 | — | 153-154 | MH+ 557 r.t. 6.5' Method A |
| 97 | 3-methylindole | H | 1 | (2R,5S)-dimethylpiperazine | 2-methyl-5-CF3-pyridine | 1 | — | 198-200 | MH+ 498 r.t. 5.27' Method |
| 98 | 3-methylindole | H | 1 | piperazine | 2-methylquinoline | 1 | — | 213-215 | MH+ 452 r.t. 4.19' Method I |
| 99 | 7-methylbenzofuran | H | 1 | piperazine | 4-methyl-7-chloroquinoline | 1 | oxalate | 99-100 | MH+ 487 r.t. 4.18' Method I |
| 100 | 3-methylindole | H | 1 | (2R,5S)-dimethylpiperazine | 2-methyl-5-fluoropyrimidine | 1 | — | 235-237 | MH+ 449 r.t. 4.6' Method I |

-continued

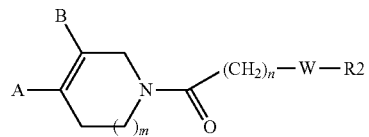

| No. | A | B | m | W | R2 | n | Salt | M.P. °C. | LCMS |
|---|---|---|---|---|---|---|---|---|---|
| 101 | 7-methylbenzothiophene | H | 1 | (2R,5S)-dimethylpiperazine | 5-chloro-2-methylpyridine | 1 | — | 157-158 | MH+ 481 r.t. 5.46' Method I |
| 102 | 7-methylbenzothiophene | H | 1 | (2R,5S)-dimethylpiperazine | 2-methylpyrimidine | 1 | — | — | MH+ 448 r.t. 4.78 Method I |
| 103 | 7-methylbenzothiophene | H | 1 | 2,5-diazabicyclo[2.2.1]heptane | 5-fluoro-2-methylpyrimidine | 1 | — | 112-113 | MH+ 464 r.t. 5.17' Method I |
| 104 | 7-methylbenzothiophene | H | 1 | piperazine | 2-methyl-6-(trifluoromethyl)pyridine | 1 | — | 74-75 | MH+ 487 r.t. 5.67' Method I |
| 105 | 7-methylbenzothiophene | H | 1 | piperazine | 2-methylquinoline | 1 | — | 177-178 | MH+ 469 r.t. 4.8' Method I |
| 106 | 7-methylbenzothiophene | H | 1 | piperazine | 7-chloro-4-methylquinoline | 1 | — | 90-91 | MH+ 503 r.t. 4.39' Method I |
| 107 | 7-methylbenzothiophene | H | 1 | piperazine | 6-chloro-2-methylpyridine | 1 | — | 92-93 | MH+ 453 r.t. 5.26' Method I |
| 108 | 3-methylindole | H | 1 | piperazine | 6-chloro-2-methylpyridine | 1 | — | 202-204 | MH+ 436 r.t. 4.67' Method I |

-continued

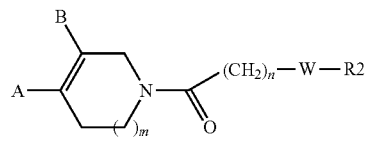

(I)

| No. | A | B | m | W | R2 | n | Salt | M.P. °C. | LCMS |
|---|---|---|---|---|---|---|---|---|---|
| 109 | 3-methylindole | H | 1 | N-methylpiperazine | 2-methyl-5-CF3-pyridine | 1 | — | 220-222 | MH+ 470 r.t. 4.93' Method I |
| 110 | 3-methylindole | H | 1 | (2S,5S)-dimethylpiperazine | 2-methylquinoline | 1 | — | 198-200 | MH+ 480 r.t. 4.45' Method I |
| 111 | 7-methylbenzothiophene | H | 1 | N,N'-dimethylhomopiperazine | 3-methylpyridine | 1 | — | — | MH+ 433 r.t. 3.62' Method I |
| 112 | 7-methylbenzothiophene | H | 1 | piperazine | 2-methyl-5,6-dichloropyridine | 1 | — | 89-90 | MH+ 487 r.t. 5.59' Method I |
| 113 | 7-methylbenzothiophene | H | 1 | piperazine | 2-methyl-6-bromopyridine | 1 | — | 80-81 | MH+ 499 r.t. 5.3' Method I |
| 114 | 2,5-dimethylbenzothiophene | H | 1 | piperazine | 2-methylquinoline | 1 | — | 189-190 | MH+ 483 r.t. 5.11' Method I |
| 115 | 7-methylbenzothiophene | H | 1 | 2,5-diazabicyclo[2.2.1] | 3-methyl-6-CF3-pyridazine | 1 | — | — | MH+ 500 r.t. 4.83' Method I |
| 116 | 2,5-dimethylbenzothiophene | H | 1 | piperazine | 2-methyl-6-CF3-pyridine | 1 | — | 121-123 | MH+ 501 r.t. 5.94' Method I |
| 117 | 2,5-dimethylbenzothiophene | H | 1 | piperazine | 4-methyl-7-chloroquinoline | 1 | — | 90-93 | MH+ 517 r.t. 4.86' Method I |

-continued

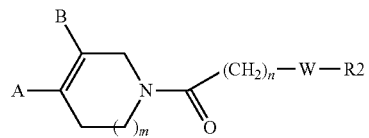
(I)

| No. | A | B | m | W | R2 | n | Salt | M.P. ° C. | LCMS |
|---|---|---|---|---|---|---|---|---|---|
| 118 | thieno[3,2-b]pyridin-4-yl methyl | H | 1 | 4-methyl-3-oxopiperazin-1-yl | 6-methyl-5-(trifluoromethyl)pyridin-3-yl | 1 | — | 145-148 | MH+ 502 r.t. 4.13' Method I |
| 119 | 7-methylbenzofuran | H | 1 | (2S,5R)-2,5-dimethylpiperazine | 6-methyl-5-(thiazol-2-yl)pyridin-3-yl | 1 | oxalate | 140-145 | MH+ 514 r.t. 5.19' Method I |
| 120 | 7-methylbenzofuran | H | 1 | (2S,5R)-2,5-dimethylpiperazine | 6-methyl-5-(2-methyl-2H-tetrazol-5-yl)pyridin-3-yl | 1 | oxalate | 165-170 | MH+ 513 r.t. 4.97' Method I |
| 121 | 2-methylquinoline | H | 1 | (2S,5R)-2,5-dimethylpiperazine | 6-methyl-5-(trifluoromethyl)pyridin-3-yl | 1 | — | 94-95 | MH+ 510 r.t. 4.95' Method I |
| 122 | 2-methylquinoline | H | 1 | 4-methyl-3-oxopiperazin-1-yl | 6-methyl-5-(trifluoromethyl)pyridin-3-yl | 1 | — | 135-136 | MH+ 496 r.t. 5.24' Method I |
| 123 | 2-methylquinoline | H | 1 | 2,5-diazabicyclo[2.2.1]heptane | 6-methyl-5-(trifluoromethyl)pyridin-3-yl | 1 | — | 101-102 | MH+ 508 r.t. 5.1' Method I |
| 124 | 7-methylbenzofuran | H | 1 | 2,5-diazabicyclo[2.2.1]heptane | 6-methyl-5-(1-methyl-1H-tetrazol-5-yl)pyridin-3-yl | 1 | — | 178-180 | MH+ 511 r.t. 4.72' Method I |
| 125 | 7-methylbenzofuran | H | 1 | (2S,5R)-2,5-dimethylpiperazine | 6-methyl-5-(methylsulfonyl)pyridin-3-yl | 1 | — | — | MH+ 509 r.t. 4.71' Method I |

The compounds according to the invention underwent biochemical studies.

Cell Culture:

The SH-SY-5Y strain (human neuroblastoma) is conventionally cultured in a DMEM culture medium (Dulbecco's Modified Eagle's Medium) (Gibco BRL, France) containing FCS (5%) (fetal calf serum) (Boehringer Mannheim, Germany), sodium pyruvate (1 mM) and glutamine (4 mM) in collagen-covered culture flasks (Becton Dickinson, France).

The SK-N-BE parent strain (human neuroblastoma) and the clone Bep 75, stably expressing the complete form of the human $p75^{NTR}$ receptor (SK-N-BE Bep 75) are conventionally cultured in an RPMI culture medium containing FCS (5%), sodium pyruvate (1 mM) and glutamine (4 mM). For the SK-N-BE Bep 75 cells, hygromycin (200 μl/20 ml of medium) is added as selection agent.

Study of the Dimerization of the $p75^{NTR}$ Receptor Independently of its Ligand The study of the dimerization of the $p75^{NTR}$ receptor is performed on a cell suspension of the strain SK-N-BE Bep 75. The cells ($2.5 \times 10^4$ cells/well) are placed in wells (96-well plate) for 24 hours, and then preincubated for 1 hour at 37° C. in the presence or absence of the compounds according to the invention. Supernatent, obtained from a culture of human cells of HEK293 renal origin expressing, after 48 hours of transfection, and secreting a soluble form of the $p75^{NTR}$ receptor (extracellular part of the receptor) coupled to an alkaline phosphatase, the latter at a final concentration of 10 nM, is then added. The quantification of the specific binding of the soluble receptor to the receptor present on SK-N-BE Bep 75 cells is determined by measuring the enzyme activity of the alkaline phosphatase after incubation of the cells for 1 hour at 37° C. in the presence of the supernatant. After filtering and transferring the filters into 24-well plates, the alkaline phosphatase activity is determined by adding CDP-Star chemoluminescent substrate (ready-to-use, Roche). The concentrations of the compounds according to the invention that inhibit 50% ($IC_{50}$) of the dimerization of the $p75^{NTR}$ receptor are low, and range from $10^{-6}$ to $10^{-11}$ M.

The compounds of formula (I) show activity in this test with $IC_{50}$ values ranging from $10^{-6}$ to $10^{-11}$ M.

For example, compounds 1, 14, 34 and 36 showed, respectively, an $IC_{50}$ value of 0.08 nM, 1.09 nM, 0.94 nM and 20 nM.

Measurement of the Apoptosis

The cells (strains of human neuroblastomas SH-SY-5Y and SK-N-BE Bep 75) are placed in Petri dishes 35 mm in diameter (Biocoat collagenI, ($10^5$ cells/well)) in a suitable culture medium containing 5% FCS, for 24 hours. The culture medium is then removed, the cells are rinsed with PBS (Dulbecco's Phosphate-buffered saline), and then either fresh medium containing 5% FCS, or medium containing NGF (at a concentration of 10 ng/ml), or beta-amyloid peptide (Aβ1-40) (at a concentration of 10 μM) is then added, in the presence or absence of the compounds according to the invention. The apoptosis levels are measured 48 hours after the treatments in the case of the strain SH-SY-5Y, and 24 hours later in the case of the strain SK-N-BE Bep 75, by quantifying the cytoplasmic histones associated with the DNA fragments (cell death detection ELISA, Boehringer Mannheim, Germany). The apoptosis levels are expressed as the amount of oligonucleosomes/$10^5$ cells. Each value corresponds to the average of 9 experimental points distributed over 3 independent experiments.

The compounds of formula (I) show activity in this test, with $IC_{50}$ values ranging from $10^{-6}$ to $10^{-11}$ M.

For example, compounds 19, 14 and 34 showed, respectively, an $IC_{50}$ value of 1.07 nM, 1.33 nM and 3.39 nM.

Thus, the binding of the compounds according to the invention to $p75^{NTR}$ receptor is reflected, firstly, at the biochemical level by inhibition of dimerization of the receptor induced by the neurotrophins, or independently of the ligand, and, secondly, at the cellular level, by inhibition of the proapoptotic effect mediated by the $p75^{NTR}$ receptor.

Thus, according to one of the subjects of the present invention, the compounds of formula (I) show very advantageous inhibitory activity on the dimerization of the $p75^{NTR}$ receptor independently of its ligand.

The compounds according to the invention may thus be used for the preparation of medicaments, in particular medicaments intended for preventing or treating any pathology in which the $p75^{NTR}$ receptor is involved, more particularly those indicated hereinbelow.

The compounds according to the invention may also be used for preventing or treating any pathology in which the $p75^{NTR}$ receptor is involved, more particularly those indicated hereinbelow.

Thus, according to another of its aspects, a subject of the invention is medicaments comprising a compound of formula (I), or an addition salt thereof with a pharmaceutically acceptable acid.

Thus, the compounds according to the invention may be used, in man or animals, in the treatment or prevention of various $p75^{NTR}$-dependent complaints such as central and peripheral neurodegenerative diseases, for instance senile dementia, epilepsy, Alzheimer's disease, Parkinson's disease, Huntington's chorea, Down's syndrome, prion diseases, amnesia, schizophrenia, depression, bipolar disorder; amyotrophic lateral sclerosis, multiple sclerosis; cardiovascular complaints, for instance post-ischemic heart damage, cardiomyopathies, myocardial infarction, cardiac insufficiency, cardiac ischemia, cerebral infarction; peripheral neuropathies (of diabetic, traumatic or iatrogenic origin); optic nerve and retinal damage (retinal pigment degeneration, glaucoma); retinal ischemia; macular degeneration, spinal cord trauma and cranial trauma; atherosclerosis; stenoses, wound healing disorders; alopecia.

The compounds according to the invention may also be used in the treatment of pancreatitis and hepatic fibrosis.

The compounds according to the invention may also be used in the treatment of cancers, for instance lung cancer, thyroid cancer, pancreatic cancer, prostate cancer, small intestine cancer, colorectal cancer and breast cancer, and in the treatment of tumors, metastases and leukemias.

The compounds according to the invention may also be used in the treatment of respiratory disorders, for instance pulmonary inflammation, allergy and asthma, and chronic obstructive pulmonary disease.

The compounds according to the invention may also be used in the treatment of cutaneous pain (of the skin, of the subcutaneous tissues and associated organs), somatic pain, visceral pain (of the circulatory, respiratory, gastrointestinal or urogenital system) and neurological pain.

The compounds according to the invention may be used in the treatment of chronic neuropathic and inflammatory pain and in the treatment of autoimmune diseases, such as rheumatoid arthritis.

The compounds according to the invention may also be used in the treatment of diseases such as ankylosing spondylitis, psoriatic arthritis and plaque psoriasis.

The compounds according to the invention may also be used in the treatment of bone fractures, and in the treatment or prevention of bone diseases such as osteoporosis.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in a unit administration form, as a mixture with standard pharmaceutical excipients, to man and animals for the treatment or prevention of the above disorders or diseases.

The appropriate unit forms of administration include oral forms such as tablets, soft or hard gel capsules, powders, granules and oral solutions or suspensions, sublingual, buccal, intratracheal, intraocular, intranasal and inhalation administration forms, topical administration forms, parenteral administration forms such as transdermal, subcutaneous, intramuscular or intravenous administration forms, rectal administration forms and implants. For topical application, the compounds according to the invention may be used in creams, gels, ointments or lotions.

By way of example, a unit form of administration of a compound according to the invention in tablet form may comprise the following components:

| Compound according to the invention | 50.0 mg |
|---|---|
| Mannitol | 223.75 mg |
| Croscaramellose sodium | 6.0 mg |
| Corn starch | 15.0 mg |
| Hydroxypropylmethylcellulose | 2.25 mg |
| Magnesium stearate | 3.0 mg |

The dose of active principle administered per day may range from 0.01 to 100 mg/kg, in one or more dosage intakes, and preferentially 0.02 to 50 mg/kg. In general, the daily dose of the compound of the invention will be the lowest effective dose of the compound that is capable of producing a therapeutic effect.

There may be particular cases in which higher or lower dosages are appropriate; such dosages do not depart from the scope of the invention. According to the usual practice, the dosage that is appropriate to each patient is determined by the doctor according to the mode of administration and the weight and response of said patient.

According to another of its aspects, the present invention also relates to a method for treating the pathologies indicated above, which comprises the administration, to a patient, of an effective dose of a compound according to the invention, or a pharmaceutically acceptable salt thereof.

What is claimed is:

1. A method for treating a pathology selected from the group consisting of Alzheimer's disease, Parkinson's disease, and Huntington's chorea; said method comprising administering to a patient in need thereof an effective dose of a compound of formula (I):

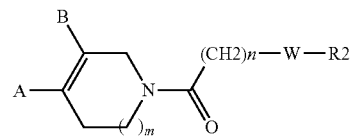

wherein:
n represents 1 or 2;
m represents 0 or 1;
A represents a fused heterocyclic group of formula (Y):

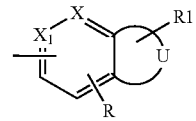

and B represents a hydrogen atom;
or
A represents a hydrogen atom; and
B represents a fused heterocyclic group of formula (Y):

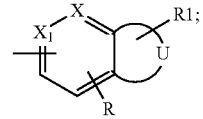

wherein the fused heterocycle of formula Y is attached to the rest of the molecule via any of the available carbon atoms,
and wherein U completes:
  either an aromatic or saturated 6-atom nucleus, containing one or two nitrogen atoms, the nucleus possibly being substituted with one or two halogen atoms, one or two (C1-C4)alkyl or (C1-C4)alkoxy groups, or one or two perfluoroalkyl radicals;
  or an aromatic or saturated 5-atom nucleus, containing a nitrogen, oxygen or sulfur atom, the nucleus optionally being substituted with one or two (C1-C4)alkyl groups;
X and X1 represent CH or N;
R and R1 are located on any of the available positions, and independently represent a hydrogen atom, a halogen atom, a group (C1-C4)alkyl, (C1-C4)alkoxy, a perfluoroalkyl or trifluoromethoxy radical, a cyano or a group COOH, COOalkyl, CONR3R4 or NHCOR3;
—W— is a nitrogenous heterocycle chosen from:

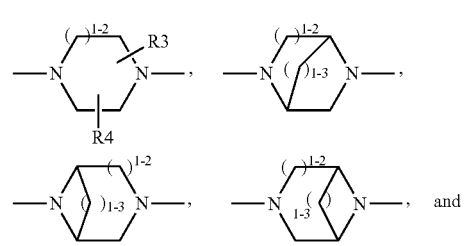

-continued

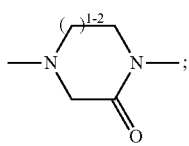

1-2 represents 1 or 2;
1-3 represents 1, 2 or 3;
R2 represents a group of formula:

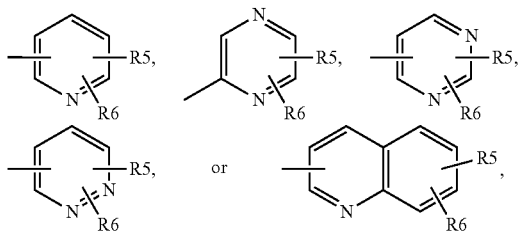

wherein R5 and R6, located on any of the available positions, independently represent a hydrogen atom, a halogen atom, a group (C1-C4)alkyl or (C1-C4)alkoxy, a trifluoromethyl or trifluoromethoxy radical, a cyano or a group COOH, COOalkyl, COOcycloalkyl, SOalkyl, SO$_2$alkyl, CONR3R4, NR3R4 or NHCOR3;
or one of R5 and R6 represents a heterocycle chosen from:

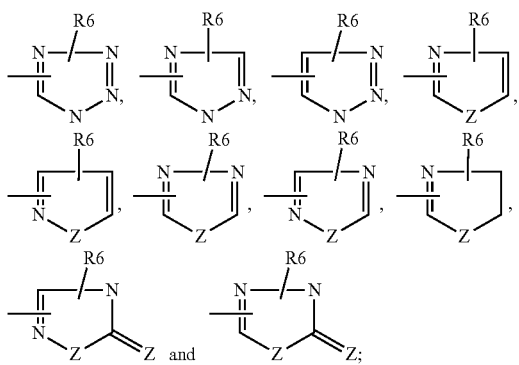

Z represents an oxygen or sulfur atom; and
R3 and R4 represent a hydrogen or a group C1-C6 alkyl;
or a pharmaceutically acceptable salt thereof.

2. The method according to claim 1, wherein for the compound of formula (I):

A represents a fused heterocyclic group of formula (Y)

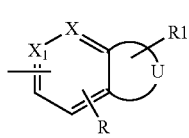

and B represents a hydrogen atom;
or
A represents a hydrogen atom;

and B represents a fused heterocyclic group of formula (Y)

(Y)

wherein the fused heterocycle of formula Y is attached to the rest of the molecule via any of the available carbon atoms of the benzene nucleus;
or a pharmaceutically acceptable salt thereof.

3. The method according to claim 1, wherein for the compound of formula (I): R and R1, located on any of the available positions, independently represent a hydrogen atom, a halogen atom or a group (C$_1$-C$_4$)alkyl or COOalkyl; or a pharmaceutically acceptable salt thereof.

4. The method according to claim 1, wherein for the compound of formula (I): —W— is a nitrogenous heterocycle chosen from:

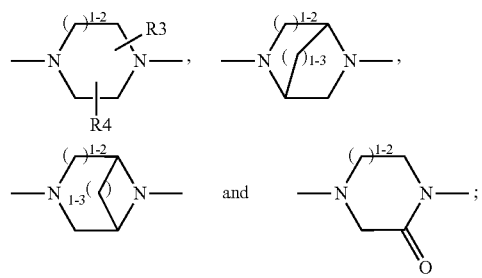

and
R3 and R4 represent a hydrogen atom or a methyl group;
or a pharmaceutically acceptable salt thereof.

5. The method according to claim 1, wherein for the compound of formula (I): R2 represents a group of formula:

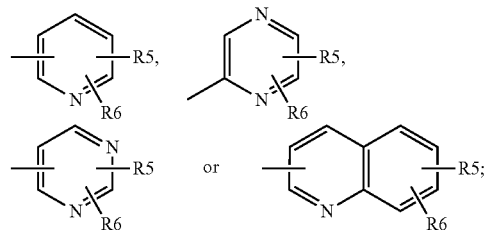

R5 and R6, located on any of the available positions, independently represent a hydrogen atom, a trifluoromethyl radical or a group COOH, COOalkyl or COOcycloalkyl;
or
one of the groups R5 and R6 represents a heterocycle chosen from:

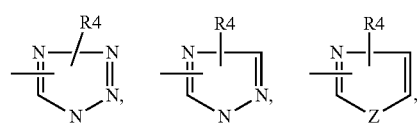

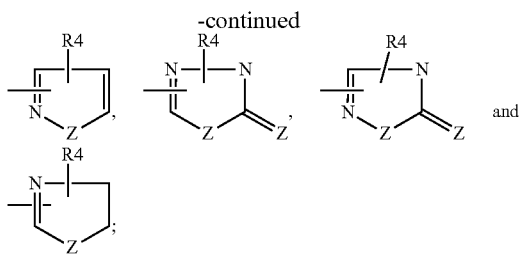

Z represents an oxygen or sulfur atom; and
R3 and R4 represent a hydrogen or a methyl group;
or a pharmaceutically acceptable salt thereof.

6. The method according to claim 1, wherein the compound of formula (I) is selected from the group consisting of:

1-(4-benzo[b]thiophen-7-yl-3,6-dihydro-2H-pyridin-1-yl)-2-(3,5-dimethyl-2,3,5,6-tetrahydro[1,2']bipyrazinyl-4-yl)ethanone;

1-(4-benzo[b]thiophen-7-yl-3,6-dihydro-2H-pyridin-1-yl)-2-(8-pyrimidin-2-yl-3,8-diazabicyclo[3.2.1]oct-3-yl)ethanone;

1-(4-benzo[b]thiophen-5-yl-3,6-dihydro-2H-pyridin-1-yl)-2-(8-pyrimidin-2-yl-3,8-diazabicyclo[3.2.1]oct-3-yl)ethanone;

1-(4-benzo[b]thiophen-7-yl-3,6-dihydro-2H-pyridin-1-yl)-2-((2S,6R)-2,6-dimethyl-4-(5-trifluoromethylpyridin-2-yl)piperazin-1-yl)ethanone;

1-(4-benzo[b]thiophen-5-yl-3,6-dihydro-2H-pyridin-1-yl)-2-((2S,5R)-2,5-dimethyl-2,3,5,6-tetrahydro[1,2']bipyrazinyl-4-yl)ethanone;

1-(4-benzo[b]thiophen-7-yl-3,6-dihydro-2H-pyridin-1-yl)-2-((2S,5R)-2,5-dimethyl-2,3,5,6-tetrahydro[1,2']bipyrazinyl-4-yl)ethanone;

1-(4-benzo[b]thiophen-5-yl-3,6-dihydro-2H-pyridin-1-yl)-2-((2S,6R)-2,6-dimethyl-4-(5-trifluoromethylpyridin-2-yl)piperazin-1-yl)ethanone;

1-(4-benzo[b]thiophen-7-yl-3,6-dihydro-2H-pyridin-1-yl)-2-[8-(5-trifluoromethylpyridin-2-yl)-3,8-diazabicyclo[3.2.1]oct-3-yl]ethanone;

1-(4-benzo[b]thiophen-7-yl-3,6-dihydro-2H-pyridin-1-yl)-2-[(2R,5S)-2,5-dimethyl-4-(5-trifluoromethylpyridin-2-yl)piperazin-1-yl]ethanone;

2-[(2S,6R)-2,6-dimethyl-4-(5-trifluoromethylpyridin-2-yl)piperazin-1-yl]-1-[4-(2-methylbenzo[b]thiophen-7-yl)-3,6-dihydro-2H-pyridin-1-yl]ethanone;

2-[(2S,6R)-2,6-dimethyl-4-(5-trifluoromethylpyridin-2-yl)piperazin-1-yl]-1-[4-(2-propylbenzo[b]thiophen-7-yl)-3,6-dihydro-2H-pyridin-1-yl]ethanone;

1-(4-benzo[b]thiophen-7-yl-3,6-dihydro-2H-pyridin-1-yl)-2-[5-(5-trifluoromethylpyridin-2-yl)-2,5-diazabicyclo[2.2.1]hept-2-yl]ethanone;

1-(4-benzo[b]thiophen-6-yl-3,6-dihydro-2H-pyridin-1-yl)-2-[(2R,5S)-2,5-dimethyl-4-(5-trifluoromethylpyridin-2-yl)piperazin-1-yl]ethanone;

1-(4-benzofuran-7-yl-3,6-dihydro-2H-pyridin-1-yl)-2-[(2R,5S)-2,5-dimethyl-4-(5-trifluoromethylpyridin-2-yl)piperazin-1-yl]ethanone;

1-[4-(2-methylbenzo[b]thiophen-5-yl)-3,6-dihydro-2H-pyridin-1-yl]-2-(8-pyrimidin-2-yl-3,8-diazabicyclo[3.2.1]oct-3-yl)ethanone;

1-[4-(2-methylbenzo[b]thiophen-5-yl)-3,6-dihydro-2H-pyridin-1-yl]-2-[4-(5-trifluoromethylpyridin-2-yl)piperazin-1-yl]ethanone;

4-{2-[4-(2-methylbenzo[b]thiophen-5-yl)-3,6-dihydro-2H-pyridin-1-yl]-2-oxoethyl}-1-(5-trifluoromethylpyridin-2-yl)piperazin-2-one;

2-[(2S,6R)-2,6-dimethyl-4-(5-trifluoromethylpyridin-2-yl)piperazin-1-yl]-1-[4-(2-methylbenzo[b]thiophen-5-yl)-3,6-dihydro-2H-pyridin-1-yl]ethanone;

1-(4-benzo[b]thiophen-7-yl-3,6-dihydro-2H-pyridin-1-yl)-2-((2S,6R)-2,6-dimethyl-4-quinolin-2-ylpiperazin-1-yl)ethanone;

1-(4-quinolin-8-yl-3,6-dihydro-2H-pyridin-1-yl)-2-[4-(5-trifluoromethylpyridin-2-yl)piperazin-1-yl]ethanone;

1-[4-(2,3-dihydrobenzo[1,4]dioxin-6-yl)-3,6-dihydro-2H-pyridin-1-yl]-2-[4-(5-trifluoromethylpyridin-2-yl)piperazin-1-yl]ethanone;

2-[8-(5-fluoropyrimidin-2-yl)-3,8-diazabicyclo[3.2.1]oct-3-yl]-1-[4-(2-methylbenzo[b]thiophen-5-yl)-3,6-dihydro-2H-pyridin-1-yl]ethanone;

1-(4-benzofuran-7-yl-3,6-dihydro-2H-pyridin-1-yl)-2-[8-(5-fluoropyrimidin-2-yl)-3,8-diazabicyclo[3.2.1]oct-3-yl]ethanone;

1-[4-(2,3-dihydrobenzo[1,4]dioxin-6-yl)-3,6-dihydro-2H-pyridin-1-yl]-2-[8-(5-fluoropyrimidin-2-yl)-3,8-diazabicyclo[3.2.1]oct-3-yl]ethanone;

2-[8-(5-fluoropyrimidin-2-yl)-3,8-diazabicyclo[3.2.1]oct-3-yl]-1-(4-thieno[3,2-c]pyridin-4-yl-3,6-dihydro-2H-pyridin-1-yl)ethanone;

1-(4-benzofuran-3-yl-3,6-dihydro-2H-pyridin-1-yl)-2-[8-(5-fluoropyrimidin-2-yl)-3,8-diazabicyclo[3.2.1]oct-3-yl]ethanone;

2-[8-(5-fluoropyrimidin-2-yl)-3,8-diazabicyclo[3.2.1]oct-3-yl]-1-[4-(1H-indol-3-yl)-3,6-dihydro-2H-pyridin-1-yl]ethanone;

1-[4-(6-fluoro-1H-indol-3-yl)-3,6-dihydro-2H-pyridin-1-yl]-2-[8-(5-fluoropyrimidin-2-yl)-3,8-diazabicyclo[3.2.1]oct-3-yl]ethanone;

1-(4-benzo[b]thiophen-3-yl-3,6-dihydro-2H-pyridin-1-yl)-2-[8-(5-fluoropyrimidin-2-yl)-3,8-diazabicyclo[3.2.1]oct-3-yl]ethanone;

4-{2-[4-(1H-indol-3-yl)-3,6-dihydro-2H-pyridin-1-yl]-2-oxoethyl}-1-(5-trifluoromethylpyridin-2-yl)piperazin-2-one;

4-[2-(4-benzo[b]thiophen-7-yl-3,6-dihydro-2H-pyridin-1-yl)-2-oxoethyl]-1-(5-trifluoromethylpyridin-2-yl)piperazin-2-one;

4-[2-(4-benzofuran-7-yl-3,6-dihydro-2H-pyridin-1-yl)-2-oxoethyl]-1-(5-trifluoromethylpyridin-2-yl)piperazin-2-one;

1-(4-benzofuran-7-yl-3,6-dihydro-2H-pyridin-1-yl)-2-[4-(5-trifluoromethylpyridin-2-yl)piperazin-1-yl]ethanone;

1-(4-benzofuran-7-yl-3,6-dihydro-2H-pyridin-1-yl)-2-[(2S,6R)-2,6-dimethyl-4-(5-trifluoromethylpyridin-2-yl)piperazin-1-yl]ethanone;

1-(4-benzofuran-7-yl-3,6-dihydro-2H-pyridin-1-yl)-2-((2S,6R)-2,6-dimethyl-4-pyrimidin-5-ylpiperazin-1-yl)ethanone;

1-(4-benzofuran-7-yl-3,6-dihydro-2H-pyridin-1-yl)-2-[(2S,6R)-4-(5-fluoropyrimidin-2-yl)-2,6-dimethylpiperazin-1-yl]ethanone;

1-(4-benzofuran-7-yl-3,6-dihydro-2H-pyridin-1-yl)-2-[(2S,6R)-2,6-dimethyl-4-(6-trifluoromethylpyridin-3-yl)piperazin-1-yl]ethanone;

2-[(2S,6R)-4-(5-fluoropyrimidin-2-yl)-2,6-dimethylpiperazin-1-yl]-1-[4-(2-methylbenzo[b]thiophen-5-yl)-3,6-dihydro-2H-pyridin-1-yl]ethanone;

2-[(2S,6R)-2,6-dimethyl-4-(6-trifluoromethylpyridin-3-yl)piperazin-1-yl]-1-[4-(2-methylbenzo[b]thiophen-5-yl)-3,6-dihydro-2H-pyridin-1-yl]ethanone;

2-((2S,6R)-2,6-dimethyl-4-pyrimidin-5-ylpiperazin-1-yl)-1-[4-(2-methylbenzo[b]thiophen-5-yl)-3,6-dihydro-2H-pyridin-1-yl]ethanone;

1-(4-benzo[b]thiophen-5-yl-3,6-dihydro-2H-pyridin-1-yl)-2-((2S,6R)-2,6-dimethyl-4-pyrimidin-5-ylpiperazin-1-yl)ethanone;

1-(4-benzo[b]thiophen-5-yl-3,6-dihydro-2H-pyridin-1-yl)-2-((2S,6R)-4-(5-fluoropyrimidin-2-yl)-2,6-dimethylpiperazin-1-yl)ethanone;

4-[2-(4-benzo[b]thiophen-5-yl-3,6-dihydro-2H-pyridin-1-yl)-2-oxoethyl]-1-(5-trifluoromethylpyridin-2-yl)piperazin-2-one;

1-[4-(2,3-dihydrobenzo[1,4]dioxin-6-yl)-3,6-dihydro-2H-pyridin-1-yl]-2-[(2S,6R)-4-(5-fluoropyrimidin-2-yl)-2,6-dimethylpiperazin-1-yl]ethanone;

1-[4-(2,3-dihydrobenzo[1,4]dioxin-6-yl)-3,6-dihydro-2H-pyridin-1-yl]-2-[(2S,6R)-2,6-dimethyl-4-(6-trifluoromethylpyridin-3-yl)piperazin-1-yl]ethanone;

1-(4-benzo[b]thiophen-5-yl-3,6-dihydro-2H-pyridin-1-yl)-2-[4-(5-trifluoromethylpyridin-2-yl)piperazin-1-yl]ethanone;

1-(4-benzo[b]thiophen-5-yl-3,6-dihydro-2H-pyridin-1-yl)-2-[(2S,6R)-2,6-dimethyl-4-(6-trifluoromethylpyridin-3-yl)piperazin-1-yl]ethanone;

6-{(3S,5R)-4-[2-(4-benzo[b]thiophen-4-yl-3,6-dihydro-2H-pyridin-1-yl)-2-oxoethyl]-3,5-dimethylpiperazin-1-yl}nicotinic acid;

4-{2-[4-(2,3-dihydrobenzo[1,4]dioxin-6-yl)-3,6-dihydro-2H-pyridin-1-yl]-2-oxoethyl}-1-(5-trifluoromethylpyridin-2-yl)piperazin-2-one;

1-(4-benzo[b]thiophen-7-yl-3,6-dihydro-2H-pyridin-1-yl)-2-[4-(5-trifluoromethylpyridin-2-yl)piperazin-1-yl]ethanone;

Methyl 6-{(3S,5R)-4-[2-(4-benzofuran-7-yl-3,6-dihydro-2H-pyridin-1-yl)-2-oxoethyl]-3,5-dimethylpiperazin-1-yl}nicotinate;

Methyl 6-{(3S,5R)-4-[2-(4-benzo[b]thiophen-5-yl-3,6-dihydro-2H-pyridin-1-yl)-2-oxoethyl]-3,5-dimethylpiperazin-1-yl}nicotinate;

1-(4-benzo[b]thiophen-7-yl-3,6-dihydro-2H-pyridin-1-yl)-2-[(2S,6R)-4-(5-fluoropyrimidin-2-yl)-2,6-dimethylpiperazin-1-yl]ethanone;

1-(4-benzo[b]thiophen-7-yl-3,6-dihydro-2H-pyridin-1-yl)-2-[(2S,6R)-2,6-dimethyl-4-(6-trifluoromethylpyridin-3-yl)piperazin-1-yl]ethanone;

1-(4-benzo[b]thiophen-7-yl-3,6-dihydro-2H-pyridin-1-yl)-2-((2S,6R)-2,6-dimethyl-4-pyrimidin-5-ylpiperazin-1-yl)ethanone;

6-{(3S,5R)-4-[2-(4-benzo[b]thiophen-5-yl-3,6-dihydro-2H-pyridin-1-yl)-2-oxoethyl]-3,5-dimethylpiperazin-1-yl}nicotinic acid;

6-{(3S,5R)-4-[2-(4-benzofuran-7-yl-3,6-dihydro-2H-pyridin-1-yl)-2-oxoethyl]-3,5-dimethylpiperazin-1-yl}nicotinic acid;

Methyl 6-{(3S,5R)-4-[2-(4-benzo[b]thiophen-7-yl-3,6-dihydro-2H-pyridin-1-yl)-2-oxoethyl]-3,5-dimethylpiperazin-1-yl}nicotinate;

6-{(3S,5R)-4-[2-(4-benzo[b]thiophen-7-yl-3,6-dihydro-2H-pyridin-1-yl)-2-oxoethyl]-3,5-dimethylpiperazin-1-yl}nicotinic acid;

4-[2-(4-benzofuran-5-yl-3,6-dihydro-2H-pyridin-1-yl)-2-oxoethyl]-1-(5-trifluoromethylpyridin-2-yl)piperazin-2-one;

Methyl 6-((3S,5R)-3,5-dimethyl-4-{2-[4-(2-methylbenzo[b]thiophen-5-yl)-3,6-dihydro-2H-pyridin-1-yl]-2-oxoethyl}piperazin-1-yl)nicotinate;

6-((3S,5R)-3,5-dimethyl-4-{2-[4-(2-methylbenzo[b]thiophen-5-yl-)-3,6-dihydro-2H-pyridin-1-yl]-2-oxoethyl}piperazin-1-yl)nicotinic acid;

1-(5-benzofuran-7-yl-3,6-dihydro-2H-pyridin-1-yl)-2-[(2S,6R)-2,6-dimethyl-4-(5-trifluoromethylpyridin-2-yl)piperazin-1-yl]ethanone;

Ethyl 6-{(3S,5R)-4-[2-(4-benzofuran-7-yl-3,6-dihydro-2H-pyridin-1-yl)-2-oxoethyl]-3,5-dimethylpiperazin-1-yl}nicotinate;

Methyl 6-{3-[2-(4-benzofuran-7-yl-3,6-dihydro-2H-pyridin-1-yl)-2-oxoethyl]-3,8-diazabicyclo[3.2.1]oct-8-yl}nicotinate;

Methyl 7-(1-{2-[(2S,6R)-2,6-dimethyl-4-(5-trifluoromethylpyridin-2-yl)piperazin-1-yl]acetyl}-1,2,3,6-tetrahydropyridin-4-yl)benzo[b]thiophene-2-carboxylate;

Methyl 5-(1-{2-[(2S,6R)-2,6-dimethyl-4-(5-trifluoromethylpyridin-2-yl)piperazin-1-yl]acetyl}-1,2,3,6-tetrahydropyridin-4-yl)benzo[b]thiophene-2-carboxylate;

2-[(2S,6R)-2,6-dimethyl-4-(5-trifluoromethylpyridin-2-yl)piperazin-1-yl]-1-[4-(2-propylbenzo[b]thiophen-5-yl)-3,6-dihydro-2H-pyridin-1-yl]ethanone;

Methyl 6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinate;

Methyl 6-{3-[2-(4-benzo[b]thiophen-5-yl-3,6-dihydro-2H-pyridin-1-yl)-2-oxoethyl]-3,8-diazabicyclo[3.2.1]oct-8-yl}nicotinate;

6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinic acid;

2-[(2S,6R)-2,6-dimethyl-4-(5-trifluoromethylpyridin-2-yl)piperazin-1-yl]-1-[4-(7-fluorobenzofuran-5-yl)-3,6-dihydro-2H-pyridin-1-yl]ethanone;

1-[4-(2,3-dimethyl benzofuran-6-yl)-3,6-dihydro-2H-pyridin-1-yl]-2-[(2S,6R)-2,6-dimethyl-4-(5-trifluoromethylpyridin-2-yl)piperazin-1-yl]ethanone;

2-[(2S,6R)-2,6-dimethyl-4-(5-trifluoromethylpyridin-2-yl)piperazin-1-yl]-1-(4-quinolein-2-yl-3,6-dihydro-2H-pyridin-1-yl)ethanone;

1-(4-benzofuran-5-yl-3,6-dihydro-2H-pyridin-1-yl)-2-(2,3,5,6-tetrahydro[1,2']bipyrazinyl-4-yl)ethanone;

Methyl 6-{3-[2-oxo-2-(4-thieno[3,2-c]pyridin-4-yl-3,6-dihydro-2H-pyridin-1-yl)ethyl]-3,8-diazabicyclo[3.2.1]oct-8-yl}nicotinate;

Methyl 6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinate;

1-(4-benzofuran-7-yl-3,6-dihydro-2H-pyridin-1-yl)-2-(4-pyridin-3-yl-[1,4]diazepan-1-yl)ethanone;

6-{3-[2-oxo-2-(4-thieno[3,2-c]pyridin-4-yl-3,6-dihydro-2H-pyridin-1-yl)ethyl]-3,8-diazabicyclo[3.2.1]oct-8-yl}nicotinic acid;

6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinic acid;

Methyl 6-{3-[2-(3-benzofuran-7-yl-2,5-dihydropyrrol-1-yl)-2-oxoethyl]-3,8-diazabicyclo[3.2.1]oct-8-yl}nicotinate;

Methyl 6-{3-[2-(3-benzo[b]thiophen-7-yl-2,5-dihydropyrrol-1-yl)-2-oxoethyl]-3,8-diazabicyclo[3.2.1]oct-8-yl}nicotinate;

4-[2-(3-benzofuran-7-yl-2,5-dihydropyrrol-1-yl)-2-oxoethyl]-1-(5-trifluoromethylpyridin-2-yl)piperazin-2-one;

6-{3-[2-(3-benzofuran-7-yl-2,5-dihydropyrrol-1-yl)-2-oxoethyl]-3,8-diazabicyclo[3.2.1]oct-8-yl}nicotinic acid;

6-{3-[2-(4-benzo[b]thiophen-7-yl-3,6-dihydro-2H-pyridin-1-yl)-2-oxoethyl]-3,8-diazabicyclo[3.2.1]oct-8-yl}nicotinic acid;
6-{3-[2-(3-benzo[b]thiophen-7-yl-2,5-dihydropyrrol-1-yl)-2-oxoethyl]-3,8-diazabicyclo[3.2.1]oct-8-yl}nicotinic acid;
Methyl 6-(3-{2-[4-(2,3-dihydrobenzo[1,4]dioxin-6-yl)-3,6-dihydro-2H-pyridin-1-yl]-2-oxoethyl}-3,8-diazabicyclo[3.2.1]oct-8-yl)nicotinate;
2-{(3S,5R)-4-[2-(4-benzo[b]thiophen-7-yl-3,6-dihydro-2H-pyridin-1-yl)-2-oxoethyl]-3,5-dimethylpiperazin-1-yl}pyrimidine-5-carboxylic acid;
3-(6-{3-[2-(4-benzofuran-7-yl-3,6-dihydro-2H-pyridin-1-yl)-2-oxoethyl]-3,8-diazabicyclo[3.2.1]oct-8-yl}pyridin-3-yl)-4H-[1,2,4]oxadiazol-5-one;
3-(6-{3-[2-(4-benzo[b]thiophen-7-yl-3,6-dihydro-2H-pyridin-1-yl)-2-oxoethyl]-3,8-diazabicyclo[3.2.1]oct-8-yl}pyridin-3-yl)-4H-[1,2,4]oxadiazol-5-one;
6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinonitrile;
1-(4-benzofuran-7-yl-3,6-dihydro-2H-pyridin-1-yl)-2-[(2S,6R)-4-(3-chloro-5-trifluoromethylpyridin-2-yl)-2,6-dimethylpiperazin-1-yl]ethanone;
1-(4-benzofuran-7-yl-3,6-dihydro-2H-pyridin-1-yl)-2-(8-pyridin-3-yl-3,8-diazabicyclo[3.2.1]oct-3-yl)ethanone;
6-{3-[2-(4-benzofuran-7-yl-3,6-dihydro-2H-pyridin-1-yl)-2-oxoethyl]-3,8-diazabicyclo[3.2.1]oct-8-yl}nicotinonitrile;
1-(4-benzofuran-7-yl-3,6-dihydro-2H-pyridin-1-yl)-2-[5-(5-trifluoromethylpyridin-2-yl)-2,5-diazabicyclo[2.2.1]hept-2-yl]ethanone;
cyclobutyl 6-(3-{2-[4-(2-methylbenzo[b]thiophen-5-yl)-3,6-dihydro-2H-pyridin-1-yl]-2-oxoethyl}-3,8-diazabicyclo[3.2.1]oct-8-yl)nicotinate;
2-[(2S,6R)-2,6-dimethyl-4-(5-trifluoromethylpyridin-2-yl)piperazin-1-yl]-1-[4-(1H-indol-3-yl)-3,6-dihydro-2H-pyridin-1-yl]ethanone;
1-[4-(1H-indol-3-yl)-3,6-dihydro-2H-pyridin-1-yl]-2-(4-quinolin-2-ylpiperazin-1-yl)ethanone;
1-(4-benzofuran-7-yl-3,6-dihydro-2H-pyridin-1-yl)-2-[4-(7-chloroquinolin-4-yl)piperazin-1-yl]ethanone;
2-[(2S,6R)-4-(5-fluoropyrimidin-2-yl)-2,6-dimethylpiperazin-1-yl]-1-[4-(1H-indol-3-yl)-3,6-dihydro-2H-pyridin-1-yl]ethanone;
1-(4-benzo[b]thiophen-7-yl-3,6-dihydro-2H-pyridin-1-yl)-2-[(2S,6R)-4-(5-chloropyridin-2-yl)-2,6-dimethylpiperazin-1-yl]ethanone;
1-(4-benzo[b]thiophen-7-yl-3,6-dihydro-2H-pyridin-1-yl)-2-((2R,5S)-2,5-dimethyl-4-pyrimidin-2-yl-piperazin-1-yl)ethanone;
1-(4-benzo[b]thiophen-7-yl-3,6-dihydro-2H-pyridin-1-yl)-2-[8-(5-fluoropyrimidin-2-yl)-3,8-diazabicyclo[3.2.1]oct-3-yl]ethanone;
1-(4-benzo[b]thiophen-7-yl-3,6-dihydro-2H-pyridin-1-yl)-2-[8-(6-trifluoromethylpyridin-2-yl)-3,8-diazabicyclo[3.2.1]oct-3-yl]ethanone;
1-(4-benzo[b]thiophen-7-yl-3,6-dihydro-2H-pyridin-1-yl)-2-(4-quinolin-2-ylpiperazin-1-yl)ethanone;
1-(4-benzo[b]thiophen-7-yl-3,6-dihydro-2H-pyridin-1-yl)-2-[4-(7-chloro-quinolin-4-yl)piperazin-1-yl]ethanone;
1-(4-benzo[b]thiophen-7-yl-3,6-dihydro-2H-pyridin-1-yl)-2-[4-(6-chloro-pyridin-2-yl)piperazin-1-yl]ethanone;
2-[4-(6-chloropyridin-2-yl)piperazin-1-yl]-1-[4-(1H-indol-3-yl)-3,6-dihydro-2H-pyridin-1-yl]ethanone;
1-[4-(1H-indol-3-yl)-3,6-dihydro-2H-pyridin-1-yl]-2-[4-(5-trifluoromethylpyridin-2-yl)piperazin-1-yl]ethanone;
2-((2S,6R)-2,6-dimethyl-4-quinolin-2-yl-piperazin-1-yl)-1-[4-(1H-indol-3-yl)-3,6-dihydro-2H-pyridin-1-yl]ethanone;
1-(4-benzo[b]thiophen-7-yl-3,6-dihydro-2H-pyridin-1-yl)-2-(4-pyridin-3-yl[1,4]diazepan-1-yl)ethanone;
1-(4-benzo[b]thiophen-7-yl-3,6-dihydro-2H-pyridin-1-yl)-2-[4-(5,6-dichloropyridin-2-yl)piperazin-1-yl]ethanone;
1-(4-benzo[b]thiophen-7-yl-3,6-dihydro-2H-pyridin-1-yl)-2-[4-(6-bromopyridin-2-yl)piperazin-1-yl]ethanone;
1-[4-(2-methylbenzo[b]thiophen-5-yl)-3,6-dihydro-2H-pyridin-1-yl]-2-(4-quinolin-2-ylpiperazin-1-yl)ethanone;
1-(4-benzo[b]thiophen-7-yl-3,6-dihydro-2H-pyridin-1-yl)-2-[5-(6-trifluoromethylpyridazin-3-yl)-2,5-diazabicyclo[2.2.1]hept-2-yl]ethanone;
1-[4-(2-methylbenzo[b]thiophen-5-yl)-3,6-dihydro-2H-pyridin-1-yl]-2-[4-(6-trifluoromethylpyridin-2-yl)piperazin-1-yl]ethanone;
2-[4-(7-chloroquinolin-4-yl)piperazin-1-yl]-1-[4-(2-methylbenzo[b]thiophen-5-yl)-3,6-dihydro-2H-pyridin-1-yl]ethanone;
4-[2-oxo-2-(4-thieno[3,2-c]pyridin-4-yl-3,6-dihydro-2H-pyridin-1-yl)ethyl]-1-(5-trifluoromethylpyridin-2-yl)piperazin-2-one;
1-(4-benzofuran-7-yl-3,6-dihydro-2H-pyridin-1-yl)-2-[(2S,6R)-2,6-dimethyl-4-(5-thiazol-2-ylpyridin-2-yl)piperazin-1-yl]ethanone;
1-(4-benzofuran-7-yl-3,6-dihydro-2H-pyridin-1-yl)-2-{(2S,6R)-2,6-dimethyl-4-[5-(2-methyl-2H-tetrazol-5-yl)pyridin-2-yl]piperazin-1-yl}ethanone;
2-[(2S,6R)-2,6-dimethyl-4-(5-trifluoromethylpyridin-2-yl)piperazin-1-yl]-1-(4-quinolin-2-yl-3,6-dihydro-2H-pyridin-1-yl)ethanone;
4-[2-oxo-2-(4-quinolin-2-yl-3,6-dihydro-2H-pyridin-1-yl)ethyl]-1-(5-trifluoromethylpyridin-2-yl)piperazin-2-one;
1-(4-quinolin-2-yl-3,6-dihydro-2H-pyridin-1-yl)-2-[8-(5-trifluoromethylpyridin-2-yl)-3,8-diazabicyclo[3.2.1]oct-3-yl]ethanone;
1-(4-benzofuran-7-yl-3,6-dihydro-2H-pyridin-1-yl)-2-{8-[5-(1-methyl-1H-tetrazol-5-yl)pyridin-2-yl]-3,8-diazabicyclo[3.2.1]oct-3-yl}ethanone; and
1-(4-benzofuran-7-yl-3,6-dihydro-2H-pyridin-1-yl)-2-[(2S,6R)-4-(5-methanesulfonyl-pyridin-2-yl)-2,6-dimethylpiperazin-1-yl]ethanone;
or a pharmaceutically acceptable salt thereof.

* * * * *